United States Patent
Lillehoj et al.

(10) Patent No.: US 11,867,655 B2
(45) Date of Patent: Jan. 9, 2024

(54) EMBROIDERED ELECTROCHEMICAL BIOSENSORS AND RELATED METHODS

(71) Applicant: BOARD OF TRUSTEES OF MICHIGAN STATE UNIVERSITY, East Lansing, MI (US)

(72) Inventors: Peter B. Lillehoj, East Lansing, MI (US); Xiyuan Liu, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 1388 days.

(21) Appl. No.: 16/095,989

(22) PCT Filed: Apr. 28, 2017

(86) PCT No.: PCT/US2017/030063
§ 371 (c)(1),
(2) Date: Oct. 24, 2018

(87) PCT Pub. No.: WO2017/189966
PCT Pub. Date: Nov. 2, 2017

(65) Prior Publication Data
US 2019/0137436 A1 May 9, 2019

Related U.S. Application Data

(60) Provisional application No. 62/329,628, filed on Apr. 29, 2016.

(51) Int. Cl.
*G01N 27/327* (2006.01)
*A61B 5/00* (2006.01)
(Continued)

(52) U.S. Cl.
CPC ....... *G01N 27/3277* (2013.01); *A61B 5/6804* (2013.01); *C12Q 1/006* (2013.01);
(Continued)

(58) Field of Classification Search
CPC ........... G01N 27/3277; G01N 27/3272; A61B 5/6804; A61B 5/68; A61B 5/6801;
(Continued)

(56) References Cited

FOREIGN PATENT DOCUMENTS

| CN | 104280444 A | 1/2015 | |
|----|----|----|----|
| KR | 20150010693 A | * 1/2015 | ........ H01M 8/0271 |

OTHER PUBLICATIONS

Choudhary et al., Lab Chip, 2015, 2064. (Year: 2015).*
(Continued)

*Primary Examiner* — Gurpreet Kaur
(74) *Attorney, Agent, or Firm* — MARSHALL, GERSTEIN & BORUN LLP

(57) ABSTRACT

The disclosure relates to textile biosensors and related systems that can be used for in situ health monitoring and disease detection. The biosensors include a flexible or textile substrate, a working electrode embroidered thereon, a reference electrode embroidered thereon, optionally a counter electrode embroidered thereon, and an enzyme probe bound to the working electrode. The biosensors can be integrated directly onto fabrics and garments to provide lightweight, unobtrusive wearable sensing systems that do not compromise wearer mobility, comfort or attention.

31 Claims, 9 Drawing Sheets

(51) Int. Cl.
  *C12Q 1/00* (2006.01)
  *G01N 27/30* (2006.01)
(52) U.S. Cl.
  CPC ....... *G01N 27/301* (2013.01); *G01N 27/3272* (2013.01); *C12Y 101/03004* (2013.01); *C12Y 113/12004* (2013.01)
(58) Field of Classification Search
  CPC .................. A61B 5/6802; C12Q 1/006; C12Y 101/03004; C12Y 113/12004
  See application file for complete search history.

(56) References Cited

OTHER PUBLICATIONS

English Machine Translation of KR20150010693 (Year: 2015).*
Seesaard et al., Sensors, 2015, 15, 1885-1902 (Year: 2015).*
International Application No. PCT/US2017/030063, International Search Report and Written Opinion, dated Jul. 17, 2017.
Rai, Hybrid Nanostructured Textile Bioelectrode for Unobtrusive Health Monitoring, A dissertation submitted in partial fulfillment of the requirements for the degree of Doctor of Philosophy in Biological Engineering, University of Arkansas (Aug. 2013).
Liu, X. et al., "Embroidered Electrochemical Sensors for Biomolecular Detection," *Lab Chip*, 16:2093-98 (2016) (published Apr. 29, 2016 online).
Liu, X. et al., "Embroidered Electrochemical Sensors on Gauze for Rapid Quantification of Wound Biomarkers," *Biosens Bioelectron*, 98:189-194 (2017) (available online Jun. 28, 2017).

* cited by examiner

EMBROIDERED ELECTROCHEMICAL BIOSENSORS AND RELATED METHODS

CROSS REFERENCE TO RELATED APPLICATION

This is a US national stage of International Patent Application No. PCT/US17/30063, filed Apr. 28, 2017, which claims priority to U.S. Application No. 62/329,628 filed Apr. 29, 2016, which is incorporated herein in its entirety.

STATEMENT OF GOVERNMENT INTEREST

This invention was made with government support under ECCS-1350560 awarded by the National Science Foundation. The government has certain rights in the invention.

BACKGROUND OF THE DISCLOSURE

Field of the Disclosure

The disclosure relates to textile biosensors and related systems that can be used for in situ health monitoring and disease detection. The biosensors can be integrated directly onto fabrics and garments to provide lightweight, unobtrusive wearable sensing systems that do not compromise wearer mobility, comfort or attention.

Background

The current capabilities of wearable sensor technology are limited to measuring physiological parameters (e.g. heart rate, blood pressure, respiratory rate) and little attention has been directed toward wearable sensors for biomolecular detection.

SUMMARY

This disclosure relates to self-powered textile biosensors utilizing a bio-micro-electromechanical system (bioMEMS) platform, which can provide wearable sensing and point-of-care diagnostics. The textile biosensors further can support healthcare and improve human well-being by (1) providing an economical means for continuous health monitoring, (2) supporting preventive medicine through early disease detection, (3) reducing healthcare costs and its burden on world economies, and (4) offering low cost diagnostics suitable for use in resource-limited countries.

In one embodiment, the disclosure relates to an embroidered electrochemical sensor for detecting a target analyte, the sensor comprising: (a) a flexible substrate; (b) a working electrode (WE) embroidered on the flexible substrate, the working electrode comprising a first (flexible) textile fiber core and a first electrically conductive material shell around the first textile fiber core; (c) (optionally) a counter electrode (CE) embroidered on the flexible substrate and spaced apart from the working electrode, the counter electrode comprising a second (flexible) textile fiber core and a second electrically conductive material shell around the second textile fiber core (e.g., the counter electrode can be omitted in a 2-electrode sensor system); (d) a reference electrode (RE) embroidered on the flexible substrate and spaced apart from both the working electrode and the counter electrode, the reference electrode comprising a third (flexible) textile fiber core and a third electrically conductive material shell around the third textile fiber core; and (e) an enzyme probe bound to the working electrode (e.g., physically adsorbed, covalently bound, etc. on an outer/exposed surface of the working electrode/electrically conductive shell thereof), wherein the enzyme probe is specific to the target analyte (e.g., the probe alters the electrical conductivity of the working electrode upon reaction with the target analyte, for example via redox reaction with the target analyte, which can increase the electrical conductivity of the working electrode).

In another embodiment, the disclosure relates to an embroidered electrochemical sensor for detecting a target analyte, the sensor comprising: (a) a flexible substrate; (b) a working electrode (WE) embroidered on the flexible substrate, the working electrode comprising a first (flexible) textile fiber core and a first electrically conductive material shell around the first textile fiber core; (c) (optionally) a counter electrode (CE) embroidered on the flexible substrate and spaced apart from the working electrode, the counter electrode comprising a second (flexible) textile fiber core and a second electrically conductive material shell around the second textile fiber core (e.g., the counter electrode can be omitted in a 2-electrode sensor system); (d) a reference electrode (RE) embroidered on the flexible substrate and spaced apart from both the working electrode and the counter electrode, the reference electrode comprising a third (flexible) textile fiber core and a third electrically conductive material shell around the third textile fiber core; and (e) a capture probe (e.g., antibody, nucleic acid, aptamer, peptide) bound to the working electrode (e.g., physically adsorbed, covalently bound, etc. on an outer/exposed surface of the working electrode/electrically conductive shell thereof), wherein the capture probe is specific to the target analyte (e.g., the capture probe specifically binds to target analyte). The capture probe need not be electrically conductive or otherwise alter the electrical conductivity of the sensor electrodes when bound to target analyte. In such cases, a separate, second capture probe label (e.g., another antibody, nucleic acid, aptamer, peptide, etc.) that is capable of specifically binding to the target analyte and which is labeled with an electrically conductive moiety, such as a suitable enzyme label (e.g., enzyme/substrate combination). Example enzyme labels include enzymes such as horseradish peroxidase (HRP), urease, or alkaline phosphatase and a substrate bound thereto. The type of substrate depends on the enzyme being used. For example, HRP substrates include 3,3',5,5'-Tetramethylbenzidine (TMB), 2,2'-azinobis(3-ethylbenzothiazoline-6-sulphonic acid) (ABTS) and 3,3'-Diaminobenzidine (DAB). For alkaline phosphatase, substrates include nitroblue tetrazolium (NBT), p-nitrophenylphosphate (pNPP) and Naphthol AS-MX and TR phosphate.

In another embodiment, the disclosure relates to an embroidered electrochemical sensor for detecting a target analyte, the sensor comprising: (a) a flexible substrate; (b) a working electrode (WE) embroidered on the flexible substrate, the working electrode comprising a first (flexible) electrically conductive fiber; (c) (optionally) a counter electrode (CE) embroidered on the flexible substrate and spaced apart from the working electrode, the counter electrode comprising a second (flexible) electrically conductive fiber; (d) a reference electrode (RE) embroidered on the flexible substrate and spaced apart from both the working electrode and the counter electrode, the reference electrode comprising a third (flexible) electrically conductive fiber; and (e) an enzyme or other capture probe (e.g., antibody, nucleic acid, aptamer, peptide) bound to the working electrode, wherein the enzyme or other capture probe is specific to the target analyte. The electrically conductive fibers can be metallic fibers (silver, gold, copper, platinum, silver-coated copper, etc.) or carbon threads/fibers, for example with the same suitable ranges for electrical conductivity/resistance as described for the core/shell electrodes.

In another embodiment, the disclosure relates to a multiplexed embroidered electrochemical sensor for detecting two or more target analytes, the sensor comprising: (a) a first embroidered electrochemical sensor according to any of the disclosed embodiments, wherein the first sensor comprises a first enzyme probe specific to a first target analyte; and (b) a second embroidered electrochemical sensor according to any of the disclosed embodiments, wherein the second sensor comprises a second enzyme probe different from the first enzyme probe and specific to a second target analyte different from the first target analyte (e.g., and so on for third, fourth, etc. distinct probe/analyte combinations in a multiplexed sensor); wherein the flexible substrate of the first sensor can be the same or different from that of the second sensor (e.g., the electrodes of each sensor can be embroidered on the same substrate or they can be embroidered on different substrates, such as for incorporation into the same garment).

In another embodiment, the disclosure relates to an multiplexed embroidered electrochemical sensor kit for detecting two or more target analytes, the kit comprising: (a) a first embroidered electrochemical sensor according to any of the disclosed embodiments, wherein the first sensor comprises a first flexible substrate and a first enzyme probe specific to a first target analyte; and (b) a second embroidered electrochemical sensor according to any of the disclosed embodiments, wherein the second sensor comprises a second flexible substrate separate from the first flexible substrate and a second enzyme probe different from the first enzyme probe and specific to a second target analyte different from the first target analyte (e.g., and so on for third, fourth, etc. distinct probe/analyte combinations in a multiplexed sensor).

In another embodiment, the disclosure relates to a method for detecting a target analyte, the method comprising: (a) providing the embroidered electrochemical sensor according to any of the disclosed embodiments; (b) applying a sample containing or suspected of containing the target analyte to the working electrode and allowing sufficient time for reaction of any target analyte with the enzyme probe (e.g., thereby altering the electrical conductivity of the working electrode); and (c) electrochemically detecting the target analyte, if present.

While the disclosed compounds, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

FIG. 3 further includes amperometric measurements of glucose (panel b) and lactate (panel c) in buffer. Values are averaged over the final 10 sec of the detection signal. Each data point represents the mean±standard deviation (SD) of three separate measurements which were obtained using new sensors.

FIG. 3 further includes graphs illustrating the specificity of the glucose assay (panel b) and lactate assay (panel c) using glucose (5 mM), lactate (12.5 mM) and uric acid (40 mM) in PBS, and PBS (blank). FIG. 3 further includes graphs illustrating amperometric signals of a 40 nM glucose sample (panel d), 50 mM lactate sample (panel e) and 40 mM glucose+50 mM lactate sample (panel f) using the dual electrochemical sensor. Each bar represents the mean±SD of three separate measurements which were obtained using new sensors.

FIG. 11 further includes images of an embroidered sensor before (panel d) and after (panel e) stretching, and corresponding cyclic voltammetry measurements (panel f).

DETAILED DESCRIPTION

The disclosure relates to textile biosensors and related systems that can be used for in situ health monitoring and disease detection. The biosensor includes electrodes formed from electrically conductive, flexible fibers that can be integrated directly onto fabrics and garments to provide lightweight, unobtrusive wearable sensing systems that do not compromise wearer mobility, comfort or attention. The biosensor can be self-powered utilizing a bio-micro-electromechanical system (bioMEMS) platform, which can provide wearable sensing and point-of-care diagnostics. The biosensor is selective for the detection of its particular target analyte, for example a chemical or biological analyte from a biofluid sample. The biosensor exhibits good resiliency against mechanical stress and superior repeatability even after deformation, which are important qualities for flexible sensor platforms, in particular wearable sensor platforms subject to folding, bending, etc. during normal use. In some embodiments, the biosensors can be used in other than wearable sensor platforms, for example in an in vitro diagnostic platform, such as a disposable embroidered biosensor for a desired analyte (e.g., a disposable glucose textile substrate biosensor).

Sensor

Figure 2:
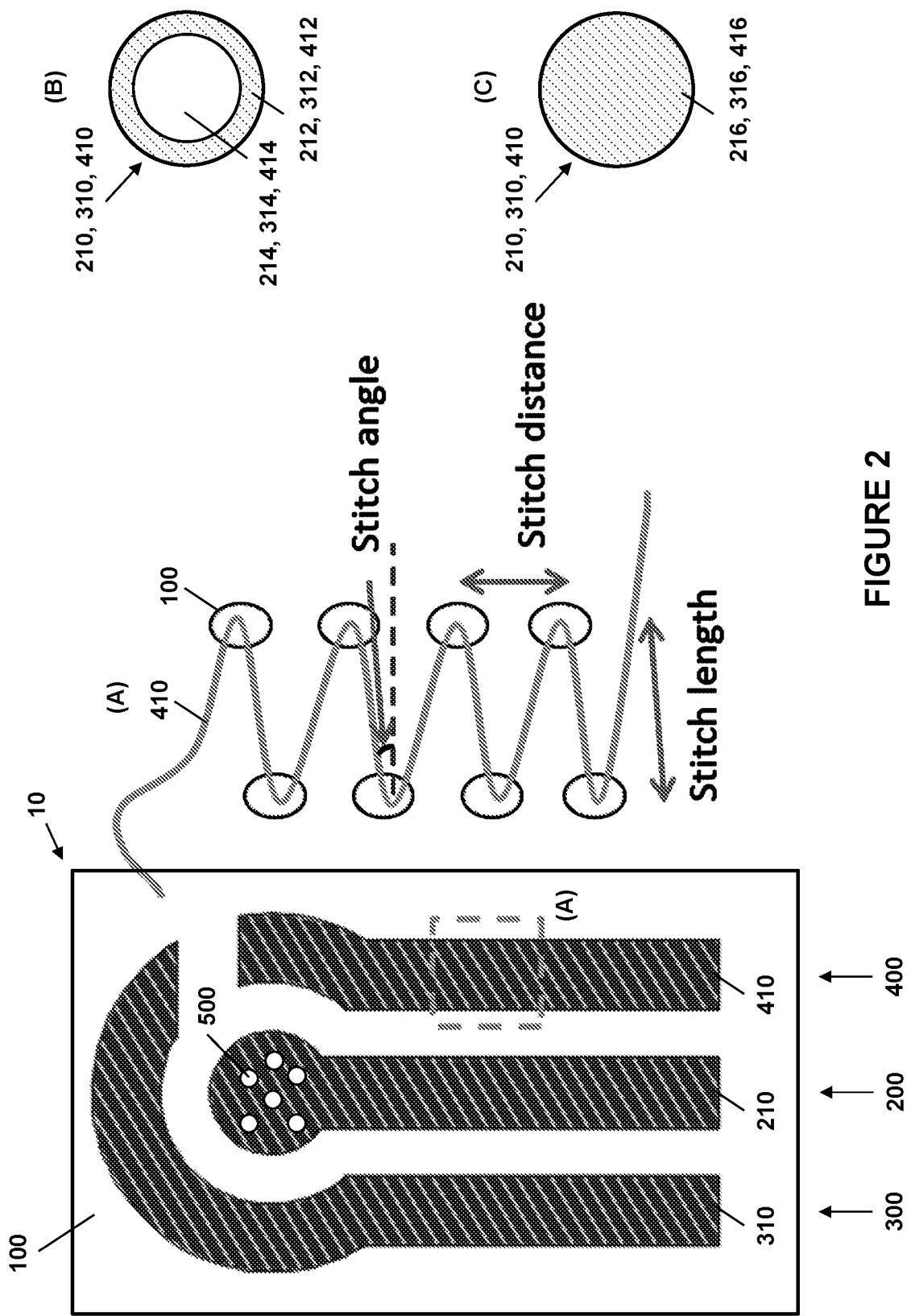
FIG. 2 is a schematic of an embroidered electrochemical sensor according to the disclosure along with insets illustrating (A) various stitch parameters for an embroidered electrode, (B) a cross sectional view of a textile fiber core/electrically conductive shell fiber structure, and (C) a cross sectional view of an electrically conductive fiber.

An embroidered electrochemical sensor (or biosensor) 10 for detecting a (biological) target analyte according to the disclosure is illustrated in FIG. 2. The sensor 10 includes flexible (textile) substrate 100 which serves as a platform for the sensor's electrodes. FIG. 2 illustrates a 3-electrode sensor 10, which includes a working electrode (WE) 200, a counter electrode (CE) 300, and a reference electrode (RE) 400. In another embodiment (not shown), the sensor 10 can be 2-electrode system including the working electrode 200 and the reference electrode 400, but omitting the optional counter electrode 300. Each of the electrodes 200, 300, 400 is embroidered on the flexible substrate 100 using flexible, electrically conductive fibers, for example a first electrically conductive fiber 210 for the working electrode 200, a second electrically conductive fiber 310 for the counter electrode 300 (when present), and a third electrically conductive fiber 410 for the reference electrode 400. The sensor 10 further includes a detection moiety 500 on the working electrode 300. The detection moiety 500 can be bound to the working electrode 300 (e.g., an exposed surface thereof), such as physically adsorbed, covalently bound, etc. on an outer/exposed surface of the working electrode 300 (e.g., on an outer or shell surface of the electrically conductive fiber 310). The detection moiety 500 is specific to a target analyte to be detected, for example being able to specifically react with the target analyte and/or being able to specifically bind to the target analyte, thus allowing detection of the target analyte in a sample applied to the sensor 10 or working electrode 300 thereof.

In some embodiments, the flexible substrate 100 is a textile substrate. The specific type of textile material for the substrate is not particularly limited, for example including animal-based textile materials, plant-based textile materials, synthetic textile materials, and combinations thereof (e.g., textile blends). Examples specific textile materials for the substrate include wools, cottons, denim, silk, satin, bamboo, polyesters, leather, artificial (faux) leather, polyacrylonitrile (e.g., acrylic textiles), polyamides (e.g., aliphatic polyamides such as nylons; aromatic polyamides such as aramids), polyurethanes (e.g., spandex, lycra), polyolefins, polychloroprenes (e.g., neoprene), and combinations or blends thereof. In some cases, the textile substrate is a component of or attached to a garment or wearable item. Examples of such garments or wearable items include arm bands, head bands, shirts, pants, undergarment (underwear, bra), socks, helmets, and shoes. The garment or wearable item can be leisure wear, sportswear or a sporting equipment/uniform, personal protective gear such as for sporting or military applications, outerwear (e.g., jackets, coats, gloves, scarves), hats, gauze, bandages, adult diapers and incontinence products, urine detection packs (e.g., for aircrew and astronauts), feminine hygiene products, and other medical garments. When attached to or provided as a component of a garment or wearable item, the sensor 10 can provide a means for detection of the target analyte upon contact with a sample fluid or other material that might contain the target analyte, for example in a fluid or other material produced or excreted by the wearer, or in a fluid or other material that contacts the wearer from an external source.

FIG. 2 (panel a) illustrates representative geometric stitch parameters for the third electrically conductive fiber 410, although the same parameters generally apply to and can be independently selected for each of the electrically conductive fibers 210, 310, 410. Stitch angle, stitch distance, and stitch angle each can be selected as desired based on the desired physical size of the corresponding sensor 10 electrode, the nature of the underlying substrate 100, the desired electrical resistivity/conductivity properties of the electrode, and the ability to conform/adapt to deformation of the substrate 100 without substantially degrading the electrical properties of the sensor 10. In some embodiments, the stitch angle can be at least 20°, 25°, 30°, or 35° and/or up to 40°, 45°, 50°, or 60°, for example 20° to 60° or 30° to 45°, which angles can improve stitch strain and embroidery quality without damage or deformation to the underlying substrate 100. In some embodiments, the stitch distance can be at least 0.05, 0.1, 0.2, or 0.3 mm and/or up to 0.2, 0.3, 0.4, or 0.6 mm, for example 0.1 mm to 0.3 mm. In some embodiments, the stitch length can be at least 0.2, 0.3, 0.4, or 0.6 mm and/or up to 0.5, 0.6, 0.8, or 1 mm, for example 0.4 mm to 0.6 mm. Selection of suitable stitch distance and/or stitch length values can promote electrode uniformity and control/reduce electrical resistance thereof.

In some embodiments, one or more of the electrically conductive fibers 210, 310, 410 used to form one or more of the electrodes 200, 300, 400 can have a core/shell structure with a textile core (e.g., as a relatively non-electrically conducting material) and an electrically conductive material as outer surface shell material. For example, as illustrated in FIG. 2 (panel b), the first electrically conductive fiber 210 can have a first (flexible) textile fiber core 214 and a first electrically conductive material shell 212 around the first textile fiber core 214. Likewise, the second electrically conductive fiber 310 can have a second (flexible) textile fiber core 314 and a second electrically conductive material shell 312 around the first textile fiber core 314, and the third electrically conductive fiber 410 can have a third (flexible) textile fiber core 414 and a third electrically conductive material shell 412 around the third textile fiber core 414.

The materials for the textile fiber cores 214, 314, 414 are not particularly limited, for example including animal-based textile fibers, plant-based textile fibers, synthetic textile fibers, and combinations thereof (e.g., textile fiber blends). The same or different fiber materials can selected for the fiber cores of the different electrodes. Examples specific textile materials for the fiber cores, which can be the same or different materials selected for the textile substrate, include wools, cottons, denim, silk, satin, bamboo, polyesters, leather, artificial (faux) leather, polyacrylonitrile (e.g., acrylic textiles), polyamides (e.g., aliphatic polyamides such as nylons; aromatic polyamides such as aramids), polyurethanes (e.g., spandex, lycra), polyolefins, polychloroprenes (e.g., neoprene), and combinations or blends thereof.

The materials for the electrically conductive shells 212, 312, 412 are not particularly limited, for example including metal-containing coatings, carbon-containing coatings, conductive polymer-containing coatings, and combinations thereof. The same or different electrically conductive materials can selected for the shells of the different electrodes. Example metal-containing coatings include silver, silver/silver chloride, gold, and/or platinum, such as in combination with a flux precoating. Example carbon-containing coatings include conductive carbon particulates such as carbon black. Example conductive polymer-containing coatings include substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof. In some cases, the metal-containing coating and/or the carbon-containing coating can be in the form of dried inks with the metal-containing material and/or the carbon-containing material, for example further including a binder from the dried ink. In a particular embodiment, the working electrode fiber and the counter electrode fiber each have a greater electrical resistance than that of the reference electrode, for example where first electrically conductive material shell 212 and the second electrically conductive material shell 312 each include a carbon-containing material or coating, and the third electrically conductive material shell 412 includes a metal-containing material or coating.

In some embodiments, one or more of the electrically conductive fibers 210, 310, 410 used to form one or more of the electrodes 200, 300, 400 can be formed substantially from electrically conductive materials. For example, as illustrated in FIG. 2 (panel c), the first electrically conductive fiber 210 can be formed from a first electrically conductive material 216, which can be a single fiber (e.g., as illustrated) or a plurality of aligned and/or interwoven smaller fibers (not shown). Likewise, the second electrically conductive fiber 310 can be formed from a second electrically conductive material 316, and the third electrically conductive fiber 410 can be formed from a third electrically conductive material 416. The same or different electrically conductive materials can selected for the fibers of the different electrodes. Similar to the electrically conductive shells, the electrically conductive materials 216, 316, 416 are not particularly limited, for example including metals (e.g., silver, copper, gold, platinum), carbon-containing materials (e.g., carbon fibers), conductive polymers (e.g., substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof), and combinations thereof.

In any of the various embodiments for the electrically conductive fibers 210, 310, 410 (e.g., core/shell or otherwise), the fibers can have any suitable degree of electrical conductivity and/or electrical resistance. For example, the electrically conductive fibers 210, 310, 410 can each independently have a (linear) electrical resistance of at least 0.1, 0.2, 0.5, 1, 2, 5, 10, 20, 50 or 100 $\Omega$/cm and/or up to 1, 2, 5, 10, 20, 50, 100, 200, 500, or 1000 $\Omega$/cm, for example ranging from 0.1 $\Omega$/cm to 1000 $\Omega$/cm. In some embodiments, the working electrode first electrically conductive fiber 210 and the counter electrode second electrically conductive fiber 310 each independently have a (linear) electrical resistance greater than the reference electrode third electrically conductive fiber 410 (e.g., electrical resistances in the native, as-formed form of the fibers, for example before resistance/conductivity is changed by reaction of the enzyme probe, capture probe, or other detection moiety with the target analyte). For example, the first and second electrically conductive fibers 210, 310 can each independently have a (linear) electrical resistance of at least 20, 50 or 100 $\Omega$/cm and/or up to 50, 100, 200, 500, or 1000 $\Omega$/cm, such as ranging from 20 $\Omega$/cm to 1000 $\Omega$/cm. Similarly, the third electrically conductive fiber 410 can have a (linear) electrical resistance of at least 0.1, 0.2, 0.5, 1, 2, 5, 10, or 20 $\Omega$/cm and/or up to 1, 2, 5, 10, 20, 50, or 100 $\Omega$/cm, such as ranging from 0.1 $\Omega$/cm to 100 $\Omega$/cm.

In some embodiments, the detection moiety 500 is an enzyme probe. The enzyme probe is specific to the target analyte, for example being able to specifically react with the target analyte (e.g., catalyzing a reaction with the target analyte as a reactant; such as without reacting with or catalyzing reactions with other reactants than the target analyte). For example, the enzyme probe can function to alter the electrical conductivity of the working electrode 200 upon reaction with any target analyte in contact with the enzyme probe/working electrode 200 (e.g., from a sample applied thereto). An example enzyme probe-induced reaction include redox reactions with the target analyte, which can increase the electrical conductivity of the working electrode 200. For example, the enzyme probe can include an oxidoreductase enzyme capable of catalyzing an oxidation-reduction (redox) reaction with the target analyte (e.g., forming hydrogen peroxide as a product, such as by oxidation of the target analyte as an enzyme probe substrate). In various embodiments, the enzyme probe can be glucose oxidase when the target analyte is glucose, the enzyme probe can be lactate oxidase when the target analyte is lactate (e.g., lactic acid and/or salt thereof), the enzyme probe can be uricase when the target analyte is uric acid, and the enzyme probe can be tyrosinase when the target analyte is a phenolic compound.

In some embodiments, the detection moiety 500 is a capture probe. The capture probe is specific to the target analyte, for example being able to specifically bind to the target analyte (e.g., immobilizing the target analyte on the working electrode 200). For example, the capture probe can variously be an antibody, nucleic acid, aptamer, or a peptide capable of specifically binding to the target analyte. Binding specificity (or specific binding) refers to the substantial recognition of a first molecule for a second molecule (e.g., the capture probe and the target analyte), for example a polypeptide and a polyclonal or monoclonal antibody, an antibody fragment (e.g., a Fv, single chain Fv, Fab', or F(ab')$_2$ fragment) specific for the polypeptide, enzyme-substrate interactions, and polynucleotide hybridization interactions. Preferably, the capture probe and the target analyte exhibit a substantial degree of binding specificity and do not exhibit a substantial amount of non-specific binding (i.e., non-covalent binding between molecules that is relatively independent of the specific structures of the molecules, for example resulting from factors including electrostatic and hydrophobic interactions between molecules). Suitable antibody capture probes can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b, IgG3, IgM, etc. Fragments thereof may include Fab, Fv and F(ab')$_2$, and Fab'. In addition, aggregates, polymers, and conjugates of immunoglobulins or their fragments can be used where appropriate so long as binding affinity for a particular molecule is maintained.

The capture probe need not be electrically conductive or otherwise alter the electrical conductivity of the sensor electrodes when bound to the target analyte. In such cases, a separate, second capture probe label (e.g., another antibody, nucleic acid, aptamer, peptide, etc.) that is capable of specifically binding to the target analyte and which is labeled with an electrically conductive moiety, such as a suitable enzyme label (e.g., enzyme/substrate combination). Example enzyme labels include enzymes such as horseradish peroxidase (HRP), urease, or alkaline phosphatase and a substrate bound thereto. The type of substrate depends on the enzyme being used. For example, HRP substrates include 3,3',5,5'-Tetramethylbenzidine (TMB), 2,2'-azino-bis(3-ethylbenzothiazoline-6-sulphonic acid) (ABTS) and 3,3'-Diaminobenzidine (DAB). For alkaline phosphatase, substrates include nitroblue tetrazolium (NBT), p-nitrophenylphosphate (pNPP) and Naphthol AS-MX and TR phosphate.

In some embodiments, the detection moiety 500 is another moiety or compound(s) having a target analyte-specific reactive and/or binding capability, which further alters its electrical conduction properties, thus permitting the sensor 10 to electrochemically detect the target analyte. For example, in an embodiment, the detection moiety 500 can be a pH-sensitive conductive polymer such as polyaniline, which transitions between different oxidation states having different electrical conductivities at different pH levels. Accordingly, a pH-sensitive conductive polymer can be used as the detection moiety 500 in a sensor 10 designed to measure pH as the target analyte (e.g., based on the presence of H$^+$ and/or OH$^-$ as analytes in a sample being tested for its pH value), where samples having different pH values alter the electrical conductivity of the working electrode 300, permitting corresponding electrochemical detection of sample pH. In another embodiment, the detection moiety 500 can be an ionophore (e.g., a biological or synthetic ionophore), which is capable of selectively binding a target ion (e.g., a single target ion or a plurality of particular target ions). Binding of the target ion to the ionophore correspondingly alters the electrical conductivity of the working electrode 300, permitting corresponding electrochemical detection of the target ion in the sample. Examples of suitable ionophores include an ammonium ionophore (e.g., for an ammonium ion target analyte), a sodium ionophore (e.g., for a sodium ion target analyte), a potassium ionophore (e.g., for a potassium ion target analyte), a calcium ionophore (e.g., for a calcium ion target analyte), a magnesium ionophore (e.g., for a magnesium ion target analyte), etc. In another embodiment, the detection moiety 500 is silver/silver chloride that can be used to selectively detect chloride ions via altered electrical conductivity of the corresponding electrode.

Methods of Detection

The embroidered electrochemical sensor 10 according to the disclosure can be used to detect a target analyte in a sample. The method generally includes applying a sample containing or suspected of containing the target analyte to the working electrode 200 of the sensor 10 and then allowing sufficient time for reaction and/or binding of any target analyte in the sample with the detection moiety 500. For example, when the detection moiety 500 is an enzyme probe, target analyte in the sample is allowed to react with the enzyme probe, forming a reaction product and thereby altering the electrical conductivity of the working electrode 200. Similarly, when the detection moiety 500 is a capture probe, target analyte in the sample is allowed to specifically bind or hybridize with the capture probe, forming a capture probe-analyte conjugate immobilized on the working electrode 200. The capture probe-analyte conjugate can then be labeled with any suitable electrically conductive label, such as the second capture probe label described above (e.g., an antibody or other moiety capable of specific binding to the target analyte), which further includes an electrically conducting component such as the enzyme label described above for the second capture probe label or such as any of the various metals and conductive polymers described above for the electrically conductive fibers. For example, the antibody or other specific binding moiety can be labeled with a metal or conductive polymer nanoparticle. Labeling of the capture probe-analyte conjugate with and electrically conducting component alters the electrical conductivity of the working electrode 200. For any of the various type of detection moieties 500, the resulting change in the electrical conductivity of the working electrode 200 in the presence of the target analyte allows subsequent electrochemically detection the target analyte when it is present (e.g., in the applied sample on the sensor 10 and, accordingly, in the sample more generally). In some cases, qualitative determination of the presence or absence of the target analyte is sufficient for diagnostic purposes. In some cases, the method can further include quantitatively determining the amount of the target analyte in the sample (e.g., as a result of a calibration curve of concentration vs. measured current at known/fixed voltage differential with a suitable electrochemical detection method).

Any of a variety of electrochemical detection methods may be used for detection of the target analyte using the resulting change in electrical conductivity of the working electrode 200 when the target analyte is present as compared to its absence. For example, any suitable voltammetric or amperometric technique may be used by application and measurement of suitable voltages and currents, etc. (e.g., using any suitable power source and electrical detection apparatus electrically connected to the sensor 10 electrodes).

For example, electrochemical detection can include applying a voltage differential to the sensor 10 and measuring a corresponding electrical current though the sensor. Examples include applying a fixed voltage differential and measuring a corresponding fixed current, applying a time-variable voltage differential and measuring a corresponding time-variable current such as in cyclic voltammetry. For instance, a bias potential can applied across the working electrode 200 and the reference electrode 400, and the current can be measured between working electrode 200 and the counter electrode 300. In addition to amperometry, other suitable electrochemical methods for use with the sensor include voltommetry, potentiometry, coulometry, and electrochemical impedance spectroscopy.

In some embodiments, the sensor 10 is in a flat configuration during sample application and electrochemical detection. For example, the sensor 10 may be used for detection in a relatively pristine form, not having been subjected to mechanical stress or deformation prior to use for detection.

In some embodiments, the sensor 10 is in a non-flat (or otherwise deformed) configuration during sample application and electrochemical detection. For example, the sensor 10 may be used for detection during or after use as incorporated into a garment or wearable item, where it would be subject to bending or other deformation during normal use of the garment or wearable item.

In some embodiments, the sensor 10 has undergone periodic deformation prior to sample application and electrochemical detection. For example, the sensor 10 may have been previously incorporated into a garment or wearable item, undergoing bending or other deformation during normal use of the garment or wearable item. The sensor 10 may be removed from or still incorporated into the item during analysis.

The analyte or target analyte generally includes a chemical or biological material, in a sample which is to be detected using the embroidered electrochemical sensor 10. Chemical or biological materials can include biological metabolites or other components found biological fluid or tissue, as well as living cells. Examples of suitable target analytes include glucose, lactate, and uric acid (e.g., when using an enzyme probe as the detection moiety 500). The target analyte can include a microbial or viral pathogen of interest (e.g., when using a capture probe as the detection moiety 500). In some embodiments, the sample includes one or more non-target analyte components, for example from biological fluids, components thereof, and combinations thereof (e.g., blood, sweat, urine, etc. from a human, mammal, or other animal source).

A sample generally includes an aliquot of any matter containing, or suspected of containing, the target analyte. The sample can include a liquid medium (e.g., aqueous or other medium, such as a biological fluid medium) and the sufficient time for application of a liquid sample can further include time for capillary action delivering the sample to the working electrode 200 via the sensor flexible/textile substrate 100 and/or electrode fibers 210, 310, 410. The liquid medium of the sample further can provide an electrical current pathway between all of the electrodes on the sensor, as they can be otherwise electrically isolated on a non-conductive substrate 100. The samples can include biological samples, such as samples from taken from humans or other animals (e.g., saliva, whole blood, serum, plasma, urine, tears, and the like), cell cultures, plants; environmental samples (e.g., water); and industrial samples. Samples may be required to be prepared prior to analysis according to the disclosed methods. For example, samples may require extraction, dilution, filtration, centrifugation, and/or stabilization prior to analysis. For the purposes herein, "sample" can refer to either a raw sample as originally collected or a sample resulting from one or more preparation techniques applied to the raw sample.

Specific contemplated aspects of the disclosure are herein described in the following numbered paragraphs.

1. An embroidered electrochemical sensor for detecting a target analyte, the sensor comprising: (a) a flexible substrate; (b) a working electrode (WE) embroidered on the flexible substrate, the working electrode comprising a first (flexible) textile fiber core and a first electrically conductive material shell around the first textile fiber core; (c) (optionally) a counter electrode (CE) embroidered on the flexible substrate and spaced apart from the working electrode, the counter electrode comprising a second (flexible) textile fiber core and a second electrically conductive material shell around the second textile fiber core (e.g., the counter electrode can be omitted in a 2-electrode sensor system); (d) a reference electrode (RE) embroidered on the flexible substrate and spaced apart from both the working electrode and the counter electrode, the reference electrode comprising a third (flexible) textile fiber core and a third electrically conductive material shell around the third textile fiber core; and (e) an enzyme probe bound to the working electrode (e.g., physically adsorbed, covalently bound, etc. on an outer/exposed surface of the working electrode/electrically conductive shell thereof), wherein the enzyme probe is specific to the target analyte (e.g., the probe alters the electrical conductivity of the working electrode upon reaction with the target analyte, for example via redox reaction with the target analyte, which can increase the electrical conductivity of the working electrode).

2. The sensor of paragraph 1, wherein the flexible substrate is a textile substrate.

3. The sensor of paragraph 2, wherein the textile substrate comprises a textile material selected from the group consisting of animal-based textile material, plant-based textile materials, synthetic textile materials, and combinations thereof (e.g., textile blends).

4. The sensor of paragraph 2, wherein the textile substrate comprises a textile material selected from the group consisting of wools, cottons, denim, silk, satin, bamboo, polyesters, leather, artificial (faux) leather, polyacrylonitrile (acrylic textiles), polyamides (e.g., aliphatic polyamides such as nylons; aromatic polyamides such as aramids), polyurethane (e.g., spandex, lycra), polyolefins, polychloroprene (e.g., neoprene) and combinations thereof (e.g., textile blends).

5. The sensor of paragraph 2, wherein the textile substrate is a component of or attached to a garment or wearable item (e.g., arm band, head band, shirt, pants, undergarment (underwear, bra), socks, helmet, shoes; can be leisure wear, sportswear or sporting equipment/uniform, personal protective gear such as for sporting or military applications, outerwear (jackets, coats, gloves, scarf), hats, gauze, bandages, adult diapers and incontinence products, piddle pack for aircrew and astronauts (urine detection), feminine hygiene products, medical garments).

6. The sensor of any of the preceding paragraphs, wherein the first textile fiber core, the second textile fiber core, and the third textile fiber core are independently selected from the group consisting of animal-based textile fibers, plant-based textile fibers, synthetic textile fibers, and combinations thereof (e.g., textile fiber blends).

7. The sensor of any of the preceding paragraphs, wherein the first textile fiber core, the second textile fiber core, and the third textile fiber core are independently selected from the group consisting of wools, cottons, denim, silk, satin, bamboo, polyesters, leather, artificial (faux) leather, polyacrylonitrile (acrylic textiles), polyamides (e.g., aliphatic polyamides such as nylons; aromatic polyamides such as aramids), polyurethane (e.g., spandex, lycra), polyolefins, polychrloroprene (e.g., neoprene) and combinations thereof (e.g., textile fiber blends).

8. The sensor of any of the preceding paragraphs, wherein first electrically conductive material shell, the second electrically conductive material shell, and the third electrically conductive material shell are independently selected from the group consisting of a metal-containing coating (e.g., silver, silver/silver chloride, gold, platinum; optionally in combination with a flux precoating), a carbon-containing coating (e.g., carbon particulate such as carbon black), a conductive polymer-containing coating (e.g., polyaniline, polypyrrole, etc.), and combinations thereof (e.g., where the metal-containing coating and/or the carbon-containing coating can be in the form of dried inks with the metal-containing and/or the carbon-containing material, for example further including a binder from the dried ink).

9. The sensor of any of the preceding paragraphs, wherein: (i) the first electrically conductive material shell and the second electrically conductive material shell each independently comprise a carbon-containing coating; and (ii) the third electrically conductive material shell comprises a metal-containing coating (e.g., where the working electrode fiber and the counter electrode fiber each have a greater electrical resistance than that of the reference electrode).

10. The sensor of any of the preceding paragraphs, wherein a fiber of the working electrode, a fiber of the counter electrode, and a fiber of the reference electrode each independently have a (linear) electrical resistance ranging from 0.1 $\Omega$/cm to 1000 $\Omega$cm (e.g., at least 0.1, 0.2, 0.5, 1, 2, 5, 10, 20, 50 or 100 $\Omega$cm and/or up to 1, 2, 5, 10, 20, 50, 100, 200, 500, or 1000 $\Omega$/cm).

11. The sensor of any of the preceding paragraphs, wherein a fiber of the working electrode and a fiber of the counter electrode each independently have a (linear) electrical resistance greater than that of a fiber of the reference electrode (e.g., electrical resistances in their native, as-formed form, for example before resistance/conductivity is changed by reaction of the enzyme probe with the target analyte).

12. The sensor of paragraph 11, wherein: (i) a fiber of the working electrode and a fiber of the counter electrode each independently have a (linear) electrical resistance ranging from 20 $\Omega$/cm to 1000 $\Omega$/cm (e.g., at least 20, 50 or 100 $\Omega$/cm and/or up to 50, 100, 200, 500, or 1000 $\Omega$/cm); and (ii) a fiber of the reference electrode has have a (linear) electrical resistance ranging from 0.1 $\Omega$/cm to 100 $\Omega$/cm (e.g., at least 0.1, 0.2, 0.5, 1, 2, 5, 10, or 20 $\Omega$/cm and/or up to 1, 2, 5, 10, 20, 50, or 100 $\Omega$/cm).

13. The sensor of any of the preceding paragraphs, wherein the enzyme probe comprises an oxidoreductase enzyme capable of catalyzing an oxidation-reduction (redox) reaction with the target analyte (e.g., forming hydrogen peroxide as a product, such as by oxidation of the target analyte as an enzyme probe substrate).

14. The sensor of any of the preceding paragraphs, wherein the enzyme probe comprises glucose oxidase and the target analyte is glucose.

15. The sensor of any of the preceding paragraphs, wherein the enzyme probe comprises lactate oxidase and the target analyte is lactate (e.g., lactic acid and/or salt thereof).

16. An embroidered electrochemical sensor for detecting a target analyte, the sensor comprising: (a) a flexible substrate; (b) a working electrode (WE) embroidered on the flexible substrate, the working electrode comprising a first (flexible) textile fiber core and a first electrically conductive material shell around the first textile fiber core; (c) (optionally) a counter electrode (CE) embroidered on the flexible substrate and spaced apart from the working electrode, the counter electrode comprising a second (flexible) textile fiber core and a second electrically conductive material shell around the second textile fiber core (e.g., the counter electrode can be omitted in a 2-electrode sensor system); (d) a reference electrode (RE) embroidered on the flexible substrate and spaced apart from both the working electrode and the counter electrode, the reference electrode comprising a third (flexible) textile fiber core and a third electrically conductive material shell around the third textile fiber core; and (e) a capture probe (e.g., antibody, nucleic acid, aptamer, peptide) bound to the working electrode (e.g., physically adsorbed, covalently bound, etc. on an outer/exposed surface of the working electrode/electrically conductive shell thereof), wherein the capture probe is specific to the target analyte (e.g., the capture probe specifically binds to target analyte). The embroidered electrochemical sensor can include any refinements of the preceding paragraphs.

17. An embroidered electrochemical sensor for detecting a target analyte, the sensor comprising: (a) a flexible substrate; (b) a working electrode (WE) embroidered on the flexible substrate, the working electrode comprising a first (flexible) electrically conductive fiber; (c) (optionally) a counter electrode (CE) embroidered on the flexible substrate and spaced apart from the working electrode, the counter electrode comprising a second (flexible) electrically conductive fiber; (d) a reference electrode (RE) embroidered on the flexible substrate and spaced apart from both the working electrode and the counter electrode, the reference electrode comprising a third (flexible) electrically conductive fiber; and (e) an enzyme or other capture probe (e.g., antibody, nucleic acid, aptamer, peptide) bound to the working electrode, wherein the enzyme or other capture probe is specific to the target analyte. The embroidered electrochemical sensor can include any refinements of the preceding paragraphs.

19. A multiplexed embroidered electrochemical sensor kit for detecting two or more target analytes, the kit comprising: (a) a first embroidered electrochemical sensor according to any of the preceding paragraphs, wherein the first sensor comprises a first flexible substrate and a first enzyme probe specific to a first target analyte; and (b) a second embroidered electrochemical sensor according to any of the preceding paragraphs, wherein the second sensor comprises a second flexible substrate separate from the first flexible substrate and a second enzyme probe different from the first enzyme probe and specific to a second target analyte different from the first target analyte (e.g., and so on for third, fourth, etc. distinct probe/analyte combinations in a multiplexed sensor).

20. A method for detecting a target analyte, the method comprising: (a) providing the embroidered electrochemical sensor according to any of the preceding paragraphs; (b) applying a sample containing or suspected of containing the target analyte to the working electrode and allowing sufficient time for reaction of any target analyte with the enzyme probe (e.g., thereby altering the electrical conductivity of the working electrode); and (c) electrochemically detecting the target analyte, if present.

21. The method of paragraph 20, wherein the sensor is in a flat configuration during sample application and electrochemical detection (e.g., representing use of the sensor in a pristine form).

22. The method of any of paragraphs 20-21, wherein the sensor is in a non-flat (deformed) configuration during sample application and electrochemical detection (e.g., representing use of the sensor during or after use as incorporated into a garment or wearable item).

23. The method of any of paragraphs 20-22, wherein the sensor has undergone periodic deformation prior to sample application and electrochemical detection (e.g., representing prior use of the sensor as incorporated into a garment or wearable item, where the sensor may be removed from or still incorporated into the item during analysis).

24. The method of any of paragraphs 20-23, wherein the sample contains the target analyte.

25. The method of any of paragraphs 20-24, wherein the sample comprises one or more non-target analyte components selected from the group consisting of biological fluids, components thereof, and combinations thereof (e.g., blood, sweat, urine, etc. from a human, mammal, or other animal source).

26. The method of any of paragraphs 20-25, wherein the sample comprises a liquid medium (e.g., aqueous or other medium, such as a biological fluid medium; the sufficient time for application of a liquid sample can further include time for capillary action delivering the sample to the working electrode via the sensor flexible/textile substrate and/or electrode fibers; liquid medium of sample further can provide an electrical current pathway between all of the electrodes on the sensor, as they can be otherwise electrically isolated on a non-conductive substrate).

27. The method of any of paragraphs 20-26, wherein electrochemical detection comprises applying a voltage differential to the sensor and measuring a corresponding electrical current though the sensor (e.g., applying a fixed voltage differential and measuring a corresponding fixed current; applying a time-variable voltage differential and measuring a corresponding time-variable current such as in cyclic voltammetry; for instance bias potential is applied across the WE and RE, and the current is measured between the WE and CE; in addition to amperometry, other suitable electrochemical methods for use with the sensor include voltommetry, potentiometry, coulometry, and electrochemical impedance spectroscopy;

28. The method of any of paragraphs 20-27, further comprising: (d) quantitatively determining the amount of the target analyte in the sample (e.g., as a result of a calibration curve of concentration vs. measured current at known/fixed voltage differential).

EXAMPLES

The examples illustrate the disclosed apparatus, processes, and compositions, but are not intended to limit the scope of any claims thereto.

Example 1

Electrochemical sensors are powerful analytical tools which possess the capacity for rapid detection of biomarkers in clinical specimens. While most electrochemical sensors are fabricated on rigid substrates, there is a growing need for sensors that can be manufactured on inexpensive and flexible materials. This example illustrates an embroidered electrochemical sensor that is capable of quantitative analytical measurements using raw biofluid samples. Conductive threads immobilized with enzyme probes were generated using a simple and robust fabrication process and used to fabricate flexible, mechanically robust electrodes on textiles. Measurements were performed to detect glucose and lactate in buffer and whole blood samples, which exhibited excellent specificity and accuracy. The embroidered biosensor can be readily fabricated in two-dimensional (2D) arrays for multiplexed measurements. The biosensor exhibits good resiliency against mechanical stress and superior repeatability, which are important requirements for flexible sensor platforms.

Electrochemical sensors are a promising technology for analytical measurements due to their speed, small size, and high sensitivity. Most commercial electrochemical sensors consist of screen-printed electrodes on rigid substrates such as glass or plastic. However, the use of flexible materials offers several useful advantages for point-of-care testing including lower device costs and improved disposability, which are particularly important for use in resource-limited settings. Towards this end, researchers have developed screen-printed electrochemical sensors on plastic films and paper. While these platforms are promising, plastic typically requires surface modification for capillary flow and paper suffers from limited durability. Alternatively, textile is a widely available, inexpensive material that offers capillary-based sample transport and enhanced robustness compared with paper. Furthermore, textile-based sensors and electronics offer facile integration with wearable materials and garments which can be used to develop wearable sensor systems. Recent research in wearable sensing has focused on the integration of sensors into fabrics for monitoring physiological parameters such as temperature, heart rate and respiration. With respect to chemical sensing, Wang's group has developed electrochemical sensors on fabrics for health, wound, and environmental monitoring. Diamond's group has also demonstrated wearable, textile-based electrochemical sensors for sweat analysis. While these devices are capable of performing sensitive analytical measurements, they rely on screen-printed sensors which tend to be mechanically fragile and can be challenging to integrate with textile-based electronic components. Recently, a textile-based electrochemical sensor was reported which employs conductive silk yarn woven into the fabric. This approach offers improved robustness compared with screen-printed sensors, but is limited to simple electrode geometries and substrates that are woven.

This example illustrates an embroidered electrochemical sensor on textile for quantitative analytical measurements. This unique approach employs conductive thread which can be embroidered onto various types of textiles and fabrics. Using a computerized embroidery machine, electrodes can be quickly fabricated with customized geometries and configurations to accommodate commercial or custom electrochemical instrumentation. For wearable sensing applications, sensors can be embroidered at specific locations on a garment needed for sampling or detection. This technique is also amenable to high-volume production which minimizes device costs associated with in vitro diagnostic testing. Due to the hydrophilic nature of most threads, embroidered sensors can quickly absorb liquids facilitating sample loading and improving automation. To demonstrate the functionality of this biosensor technology for point-of-care testing, several studies were performed to evaluate its specificity and accuracy for the detection of glucose and lactate in buffer and whole blood samples. The embroidered sensor can be used for multiplexed detection with high specificity and sensitivity by fabricating a sensor array for simultaneous measurements of analytes. The performance of the biosensor under repeated mechanical deformation was evaluated, which reveals its ability to generate accurate and consistent measurements under such conditions.

Biochemicals and reagents: Glucose, glucose oxidase, uric acid, and L-lactate were purchased from Sigma-Aldrich (St. Louis, MO) and lactate oxidase was purchased from A.G. Scientific (San Diego, CA). Silver/silver chloride (Ag/AgCl) and carbon inks were purchased from Conductive Compounds Inc. (Hudson, NH). Blocker Casein in PBS was purchased from Thermo Scientific (Tustin, CA). Deionized (DI) water was generated using a Barnstead SMART2PURE water purification system. For single and multi-analyte measurements in buffer samples, analytes were resolved in PBS at room temperature. Blood samples were prepared by adding analytes in human whole blood from BioreclamationIVT (Hicksville, NY). Samples were freshly prepared prior to experiments and remaining biochemicals were used without further purification.

Thread preparation: The electrochemical sensors consist of three electrodes, a reference electrode (RE), working electrode (WE) and counter electrode (CE), which were fabricated from custom conductive thread. Briefly, polyester thread (Brothers International, Bridgewater, NJ) was coated with carbon or Ag/AgCl ink and cured at 120° C. for 40 min. Thread coated with carbon ink was used for the WE and CE, and thread coated with Ag/AgCl ink was used for the RE. For Ag/AgCl thread, soldering flux (Kester, Itasca, IL) was applied to the thread using a flux pen prior to the ink coating process to minimize oxidation of the ink. Glucose oxidase or lactate oxidase was immobilized onto the WE by immersing carbon-coated thread in either a glucose oxidase (645 U/mL) or lactate oxidase (256 U/mL) solution, followed by air drying overnight at room temperature.

Thread characterization: Threads were characterized using optical microscopy (Nikon Eclipse TS100-F trinocular microscope and DS-Fi1 camera), scanning electron microscopy (SEM) and energy-dispersive X-ray spectroscopy (EDS) to study their morphology after the ink coating process. SEM images and EDS spectrum were captured using a JEOL 6620LV scanning electron microscope at 10 kV or 12 kV with 1200× and 170× magnifications for FIG. 1, panels c and d, respectively. The electrical properties of the threads were characterized by measuring their electrical resistance using a Fluke 87-V digital multimeter. Threads were cut into 1 m-long pieces and attached to the multimeter by clamping the ends using alligator clip probes.

Sensor design and fabrication: Electrodes were designed using AutoCAD software (Autodesk, Vernon Hills, IL) and converted into an embroidery file using SEWART software (S & S Computing). Several embroidery parameters, such as the stitch length and stitch density, were optimized to enhance the embroidery quality for improved signal consistency and signal-to-noise ratio (SNR). The electrodes were fabricated using a Brothers SE400 computerized embroidery machine on polyester fabric stacked with an embroidery stabilizer film (World Weidner, Ponca City, OK). After the sensors were embroidered, the stabilizer film was removed and individual sensors were cut and stored at ambient conditions prior to experiments.

Electrochemical measurements: Amperometric measurements were performed using a multichannel electrochemical workstation (GeneFluidics, Inc. Irwindale, CA). For single analyte measurements, 35 µL of sample was dispensed onto the sensing region using a pipette, followed by the application of a −200 mV bias potential after 1 min. For multi-analyte measurements, 60 µL of sample was used. All measurements were performed at room temperature under ambient conditions using new sensors.

Figure 1:
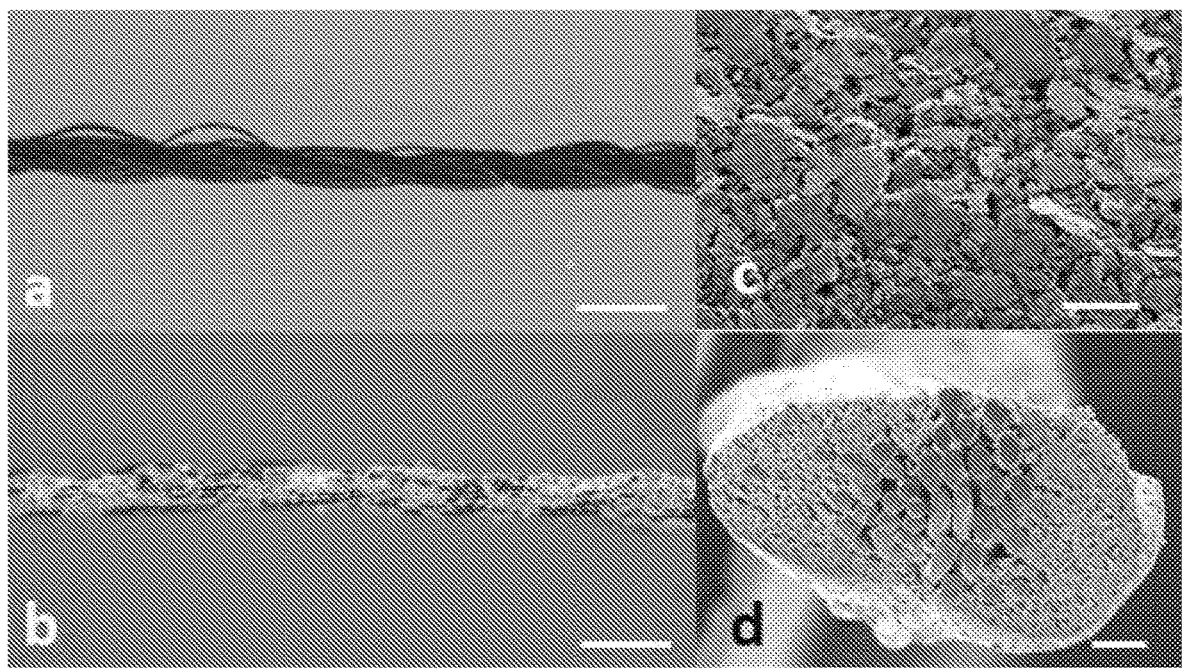
FIG. 1 includes optical images of uncoated thread (a) (scale bar, 500 µm) and Ag/AgCl-coated thread (b) (scale bar, 500 µm), as well as scanning electron microscope (SEM) images of Ag/AgCl-coated thread showing its surface morphology (c) (scale bar, 50 µm), and cross-section (d) (scale bar, 50 µm).

Characterization of ink-coated thread: Optical images of uncoated thread (FIG. 1, panel a) and Ag/AgCl-coated thread (FIG. 1, panel b) show the effects of the thread coating and enzyme immobilization process. As shown in FIG. 1, panel b, the entire length of thread is uniformly coated with Ag/AgCl with negligible blotching or defects. Similar surface coverage was also observed for carbon-coated thread. SEM was used to further observe changes in the thread surface morphology following the coating process. Magnified images of Ag/AgCl-coated thread reveal that Ag/AgCl completely fills the microscopic voids on the surface thereby improving surface coverage (FIG. 1, panel c). Cross-sectional images of the threads show that Ag/AgCl permeates into the fibers at depths of up to 50 µm (FIG. 1, panel d), which is confirmed by EDS analysis. These results also demonstrate that the enzyme immobilization process has a negligible impact on the surface morphology and the coating thickness. Since the electrical properties of the threads are strongly dependent on the quality of the ink coating, the electrical resistance of the coated threads was also measured. Ag/AgCl and carbon-coated thread exhibited resistances of ~0.8 and ~140 Ω/cm respectively, which is similar to values reported in literature. The resistance of Ag/AgCl-coated thread was significantly reduced by applying flux to the thread which helped to prevent oxidation of Ag/AgCl. The resistance of Ag/AgCl-coated thread without flux can reach as high as 80 Ω/cm.

Thread embroidery characterization: Embroidery is an intricate process where graphical patterns are sewn onto fabrics using thread. Several embroidery parameters, including stitch length and separation distance, were studied to optimize the quality of the electrodes. For instance, decreasing the stitch separation distance resulted in a higher stitch density which improved electrode uniformity. However, using a higher stitch density required a larger amount of thread which increased the electrical resistance of the electrodes. It was determined that a stitch separation distance of 0.2 mm and stitch length of 0.5 mm produced consistent uniformity while minimizing the electrode resistance. Using these optimized parameters, sensors and sensor arrays were successfully fabricated onto polyester and cotton fabrics, as well as wearable garments. Representative embroidered sensors (schematically illustrated in FIG. 2) were formed on a textile "chip" for in vitro diagnostic testing, a cotton gauze for wound monitoring, and a cotton t-shirt for sweat analysis.

Figure 3:
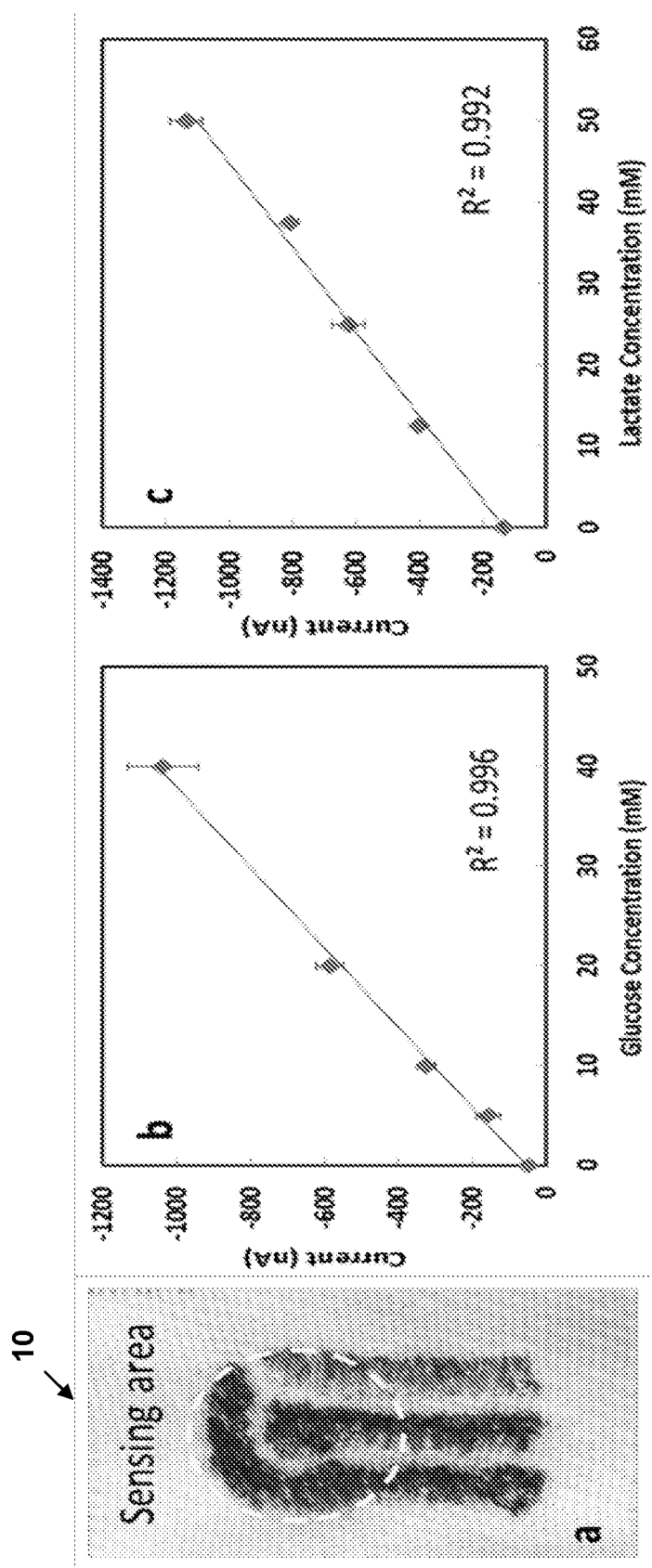
FIG. 3 includes an image of a single embroidered electrochemical sensor according to the disclosure, where the dashed circle represents the sensing area (panel a).

Single analyte detection: To demonstrate the utility of this technology for quantitative biomarker detection, measurements of glucose were performed in buffer samples. 35 µL of sample was dispensed onto the sensing area of sensor 10, as shown in FIG. 3 (panel a), which was quickly soaked up by the electrodes due to the high wettability of the thread and fabric. Measurements were performed after 1 min, which was sufficient time for the sample to be fully absorbed and generate a stable electrochemical reaction. The glucose assay exhibits a highly linear response over the entire concentration range with a $R^2$ correlation coefficient of 0.996 (FIG. 3, panel b). In addition, it exhibits very low background noise at 0 mM and very small standard deviations (SDs) of <3% over three individual measurements obtained using new sensors, which demonstrates the high accuracy and reproducibility of this assay. Measurements were also performed to detect lactate in buffer samples using sensors functionalized with lactate oxidase. Similar to the glucose assay, this assay exhibits an excellent linear response over the entire concentration range ($R^2$=0.992) and highly accurate measurements with SDs of <6%. These results show that the embroidered biosensor can quickly and accurately detect different types of analytes on a flexible, textile platform.

Figure 4:
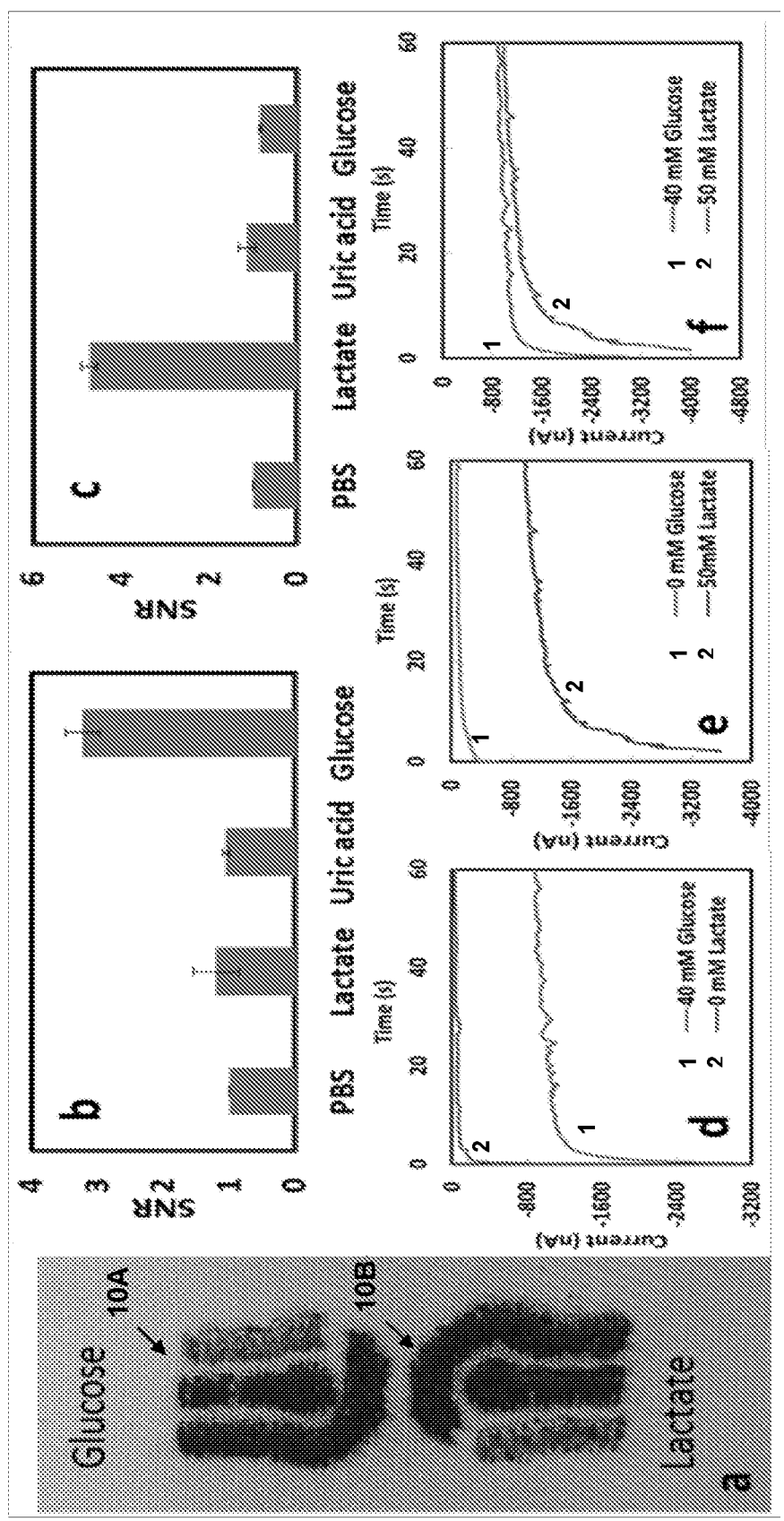
FIG. 4 includes an image of a dual electrochemical sensor for multiplexed analyte detection of glucose and lactate at separate electrode arrays (panel a).

Multiplexed detection: In addition to single analyte measurements, experiments were carried out using the embroidered biosensors for multiplexed measurements of glucose and lactate. The specificity of the individual glucose and lactate assays was tested by performing measurements using a mixture of analytes in PBS including glucose (5 mM), lactate (12.5 mM) and uric acid (40 mM). For the glucose assay, only the glucose sample generated a significant response (SNR of 3.2) compared with the irrelevant targets and blank control (FIG. 4, panel b). Similarly, the lactate assay only generated a substantial response to lactate (SNR of 4.1) with negligible signals from the nonspecific analytes (FIG. 4, panel c). These results indicate that the sensor is capable of high specificity measurements and suitable for multiplexed detection of multiple analytes with a low likelihood of interference caused by nonspecific targets.

A dual electrochemical sensor was prepared, with two sensors facing opposite to each other (FIG. 4, panel a), for simultaneous measurements of glucose and lactate. One sensor 10A was functionalized with glucose oxidase and the other sensor 10B was functionalized with lactate oxidase. Using this dual sensor, a sample containing only 40 mM of glucose was first tested. As shown in FIG. 4 (panel d), only the glucose oxidase-functionalized sensor generated a significant signal, which is consistent with the results from the individual assay measurements in FIG. 4 (panel b). In contrast, the lactate oxidase-functionalized sensor generated a negligible signal similar to that of the PBS blank control. A 50 mM lactate sample using the dual sensor was also tested, and only the lactate oxidase-functionalized sensor generated a significance response (FIG. 4, panel e), demonstrating the high specificity of the dual electrochemical sensor.

For multiplexed detection, a sample containing 40 mM glucose and 50 mM lactate was prepared and dispensed onto the dual sensor chip. Two distinct signals were simultaneously generated corresponding to the glucose and lactate targets (FIG. 4, panel f). These collective results show that the signals generated for different analytes do not interfere with each other during multiplexed measurements. By incorporating additional sensors in the array, it is possible to perform simultaneous measurements of numerous analytes from a single sample. While the dual electrochemical sensor used in this example was designed to accommodate the specific electrochemical analyzer used for detection, it is possible to design sensor arrays that can accommodate other commercial or custom electrochemical instrumentation.

Figure 5:
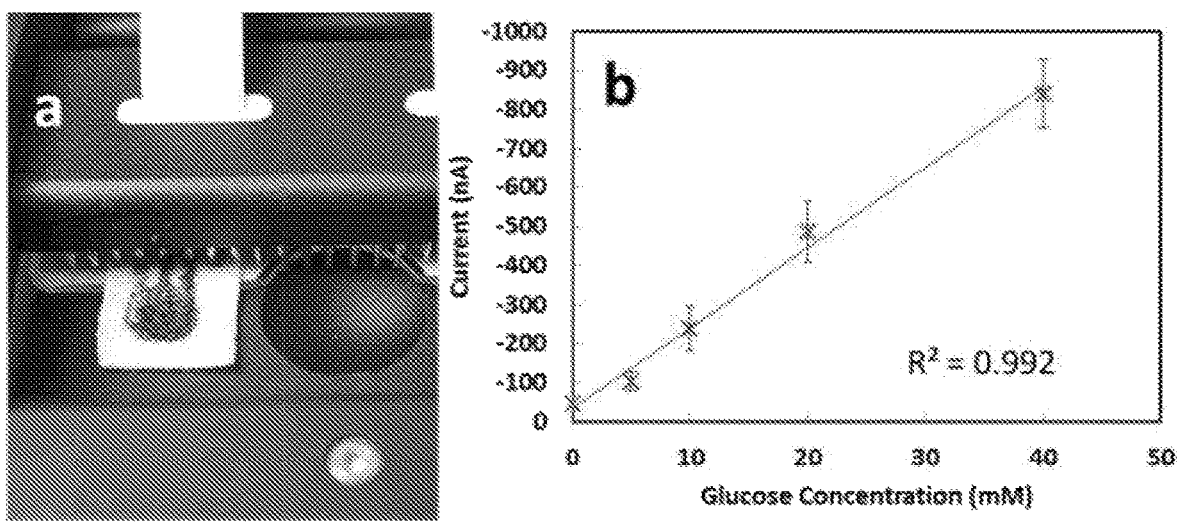
FIG. 5 illustrates an embroidered sensor according to the disclosure inside the electrochemical workstation during testing (panel a), and amperometric measurements of glucose in whole blood (panel b). Values are averaged over the final 10 sec of the detection signal. Each data point represents the mean±SD of three separate measurements which were obtained using new sensors.

Glucose detection in whole blood: To further demonstrate the utility of this sensor for biomolecular detection, its performance was tested for analyte measurements in whole blood. Blood samples spiked with glucose were dispensed on the sensor and placed in the electrochemical reader (FIG. 5, panel a). Due to the higher viscosity of blood compared with buffer, it took slightly longer (~30 sec) for the sample to completely be absorbed by the electrodes. Similar to glucose measurements in PBS, this assay exhibits a highly linear response ($R^2$=0.992) from 0 mM to 40 mM (FIG. 5, panel b), which spans the clinically relevant blood glucose concentrations in humans. Additionally, the low detection signal at 0 mM indicates that this assay generates minimal background noise even in complex biological matrices. These results show that the embroidered sensor is capable of accurate quantitative measurements of protein biomarkers in clinical samples and holds great potential for point-of-care testing.

Figure 6:
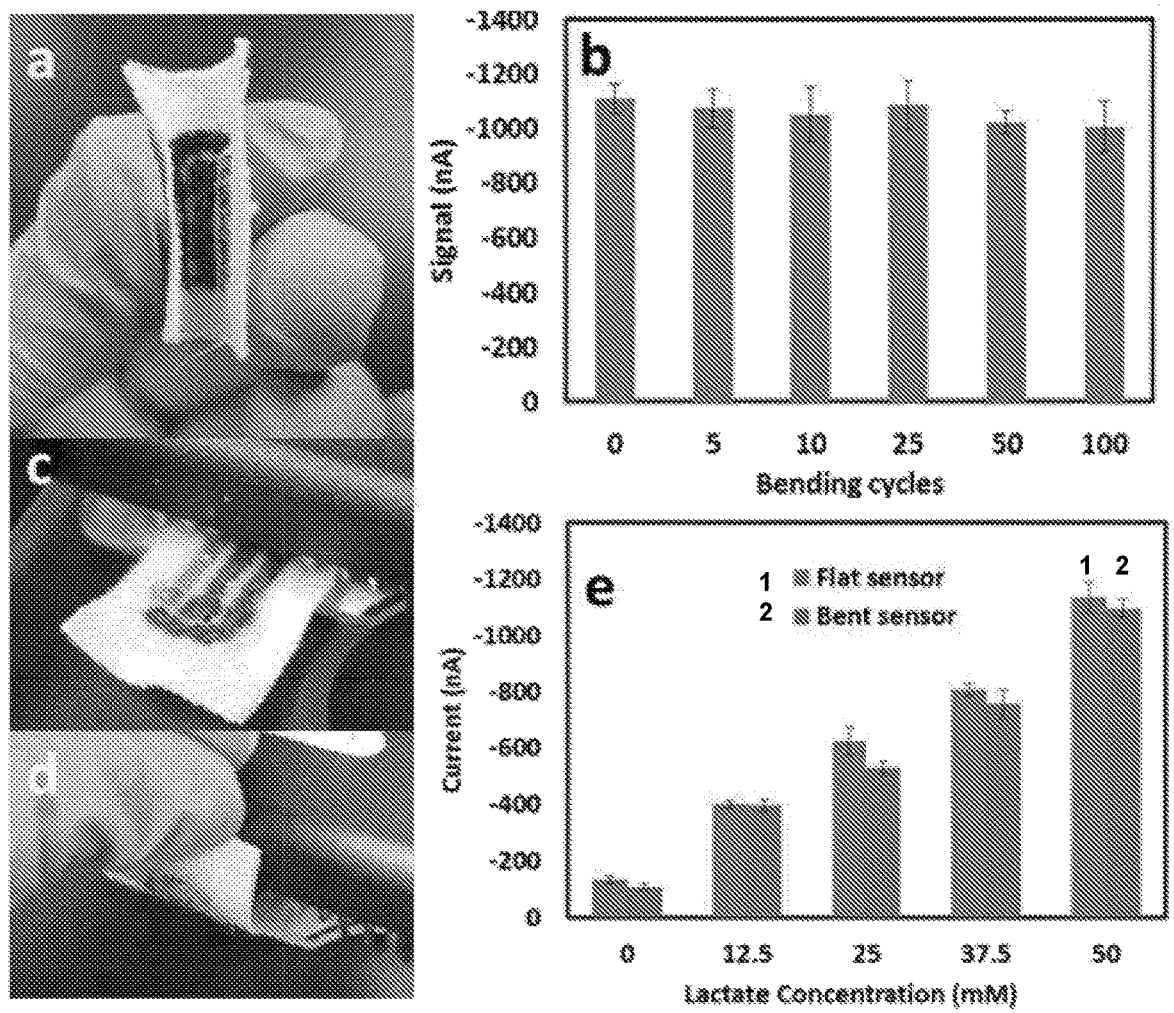
FIG. 6 illustrates mechanical bend testing of embroidered electrochemical sensors according to the disclosure (panel a), amperometric measurements of lactate (50 mM) in PBS following up to 100 cycles of bending (panel b), images of the sensor positioned flat in the reader (panel c), images of the sensor positioned and bent at 90° in the reader (panel d), and comparative measurements of lactate using flat or bent sensors. Each bar represents the mean±SD of three separate measurements (panel e).

Sensor durability testing: An important consideration for flexible sensors is the influence of mechanical deformation on the detection performance. Specifically, textile sensors are inherently susceptible to deformation (i.e. bending or folding) before and during testing and should be able to maintain detection accuracy. To mimic such effects, two studies were performed using the embroidered biosensor. In the first study, the sensor (as shown in FIG. 6, panel a) was manually folded and flattened for up to 100 cycles, and measurements of lactate samples were performed at intervals of 5, 10, 25, 50 and 100 bending cycles. By comparing the signals of sensors that underwent bending with control sensors that did not undergo deformation (FIG. 6, panel b), it is seen that there is negligible change in the signal after 25 cycles, which is a reasonable limit for in vitro diagnostic testing. Furthermore, there is only a marginal decrease of 7% and 9% in the signal after 50 and 100 cycles, respectively, which is tolerable for wearable sensing applications.

In the second study, sensor performance was examined in response to deformation occurring simultaneously while the measurement was being carried out. To experimentally mimic this scenario, measurements of lactate samples (0-50 mM) were performed using sensors which were manually bent at 90° while the signals were being recorded. Comparative signals from sensors positioned flat in the reader (FIG. 6, panel c) and mechanically bent sensors (FIG. 6, panel d) are shown in FIG. 6 (panel e). While the signal of the bent sensors slightly diminishes at concentrations above 25 mM, the signal maintains a highly linear response ($R^2$=0.981) throughout the tested concentration range, which is similar to that of the flat sensor. Additionally, both the bent and flat sensors exhibit high accuracy as represented by the low SD (<6%) of multiple measurements. These data reveal that mechanical deformation during testing has a minimal impact on the performance of the embroidered biosensor as the response from the bent sensors is nearly identical to those from the flat sensors. These results also suggest that the embroidered biosensor will be able to maintain its accuracy and reproducibly under instances of repeated deformation for in vitro diagnostic testing or wearable sensing.

Summary: This example illustrates an embroidered electrochemical sensor for quantitative biomarker measurements. This biosensor consists of electrodes fabricated from conductive threads that are subsequently embroidered onto wearable fabrics. Based on this approach, biosensor arrays can be rapidly produced with customized electrode geometries and configurations. Single analyte measurements of glucose and lactate in PBS were performed, which exhibited high specificity, a highly linear response and excellent accuracy. A dual sensor was fabricated and employed for multiplexed measurements of glucose and lactate, which exhibited similar performance as the single analyte assays. The utility of this platform for biomolecular detection was demonstrated by using it for glucose measurements in whole blood samples, which exhibited excellent performance, thereby showcasing its usefulness for clinical sample testing. Experiments to evaluate the performance of the biosensor in response to mechanical deformation showed its capability to produce consistent and accurate measurement in response to repeated folding/bending prior to and during testing. In addition to its exceptional sensing performance, the embroidered biosensor is amenable to high-volume production using existing manufacturing technologies which minimizes overall costs and enables facile integration with inexpensive and wearable materials. These collective features make the embroidered electrochemical sensors well suited for diagnostic applications requiring rapid, accurate measurements on disposable and wearable platforms. For wearable sensing applications, the sensors could be integrated with miniature sensing electronics on textiles using conductive ink or thread, and data could be transmitted wirelessly to a peripheral device (e.g., a smartphone). Further advancements in electronic textiles (e-textiles) may also enable electronics to be directly integrated into garments thereby improving device portability and user comfort.

Example 2

Wearable sensors have gained considerable attention in recent years due to their capacity for real-time health and environmental monitoring. In particular, wearable chemical sensors enable analytical measurements of bodily fluids in situ minimizing the time, labor and costs associated with conventional laboratory-based assays. Prior wearable sensors have mainly been applied for assessing overall health via monitoring analytes in bodily fluids such as sweat, tears, and interstitial fluid. Another important application where wearable sensors show promise is wound monitoring. Chronic and acute wounds are a rapidly growing public health issue and place a significant burden on the healthcare system. In the United States alone, it is estimated that chronic wounds affect 6.5 million people resulting in annual treatment costs in excess of $25 billion. One of the main challenges associated with wound management is monitoring wound status which is largely based on visual inspection and patient feedback. Therefore, researchers have been developing wearable sensors to monitor various physiological and biochemical parameters of wounds such as wound pH, bacterial metabolites, temperature, moisture and endogenous biomarkers. These devices, as well as most wearable chemical sensors, employ screen-printed electrodes which are simple to fabricate, inexpensive and offer good analytical performance. However, screen printing is poorly suited for loosely woven materials, such as gauze and wound dressing, due to their high porosity and textured surface. Furthermore, screen-printed sensors on gauze are highly susceptible to damage resulting from mechanical stress and deformation in response to the wearer's movement.

This example illustrates a gauze-based embroidered biosensor for in situ electrochemical measurements. This is made possible via a unique embroidery process which enables the fabrication of robust, flexible electrodes on loosely woven materials including gauze and wound dressing. This sensor was used for quantitative measurements of uric acid in simulated wound fluid. Uric acid is associated with oxidative stress and bacterial infection within the wound area and its levels in wound fluid is highly correlated with wound severity, which makes its a useful indicator of wound status and infection. In addition to single measurements, embroidered sensors were used for continuous measurements of uric acid for up to 7 hr demonstrating the utility of this platform for wound monitoring. This example further compare the durability of the disclosed embroidered biosensors with screen-printed biosensors, and evaluates the effects of mechanical deformation on its analytical performance.

Biochemicals and reagents: Uric acid, glucose, L-lactate, creatinine, albumin and potassium ferrocyanide ($K_3[Fe(CN)_6]$) were purchased from Sigma-Aldrich (St. Louis, MO). Uricase and Ringer's solution were purchased from Fisher Scientific (Pittsburgh, PA). Silver/silver chloride (Ag/AgCl) and carbon inks were purchased from Conductive Compounds Inc. (Hudson, NH) and Kapton was purchased from McMaster-Carr (Elmhurst, IL). Deionized (DI) water (18.3 $M\Omega\text{-cm}^{-1}$) was generated using a Barnstead SMART2PURE water purification system. PBS powder (pH 7.4) was purchased from Sigma-Aldrich (St. Louis, MO) and prepared as directed using DI water. Simulated wound fluid was freshly prepared by adding 17 g/L albumin to Ringer's solution as previously described. Analytes were serially diluted in simulated wound fluid at room temperature, and samples were freshly prepared prior to measurements.

Thread preparation: Each electrochemical sensor consists of three electrodes; a reference electrode (RE), working electrode (WE) and counter electrode (CE), which was fabricated using ink-coated thread. Briefly, polyester thread (Brothers International, Bridgewater, NJ) was soaked in carbon or Ag/AgCl ink and cured at 120° C. for 40 min. Carbon-coated thread was used for the WE and CE, and Ag/AgCl-coated thread was used for the RE. Soldering flux (Kester, Itasca, IL) was applied to the Ag/AgCl thread using a flux pen prior to the ink coating process to minimize oxidation of the ink.

Sensor design and fabrication: Sensors were designed using AutoCAD software (Autodesk, Vernon Hills, IL), converted into an embroidery file using SEWART software (S & S Computing), and embroidered onto gauze using a Brothers SE400 computerized embroidery machine. A stabilizer (World Weidner, Ponca City, OK) was used to improve the embroidery quality. Several embroidery parameters, such as the stitch length and stitch density, were optimized to enhance the electrical properties of the electrodes for improved signal consistency and SNR. After the electrodes were embroidered, the stabilizer was removed and sensors were cut into individual pieces. Screen-printed sensors were fabricated by screen printing Ag/AgCl and carbon inks onto gauze using a Kapton stencil. The stencil was designed using AutoCAD software and fabricated using a $CO_2$ laser cutter (Universal Laser Systems, Scottsdale, AZ). After screen-printing, the sensors were heated for 4 min at 120° C. and cut into individual pieces. Uricase solution (10 mg/mL) was drop cast on the WE and dried for at least 1 hr prior to measurements. Prepared sensors were used immediately or stored at ambient conditions for up to 3 days prior to experiments.

Sensor characterization: SEM was used to examine the morphology of ink-coated thread and embroidered electrodes. SEM images were captured using a JOEL 6620V scanning electron microscope at 10 kV at 30× or 5000× magnification for both the RE and WE. For sensor stretching experiments, one end of the sensor was affixed to a solid surface using a bar clamp while the other side was attached to a M&A Instruments digital force gauge using a plastic spring clamp.

Electrochemical measurements: Amperometric measurements were performed using a multichannel electrochemical workstation (GeneFluidics, Inc. Irwindale, CA). For single measurements, 15 μL of sample was dispensed from the backside of the sensor using a pipette, followed by the application of a 350 mV bias potential. Each measurement was performed using a new sensor. For uric acid monitoring, 20 μL of sample was dispensed from the backside of the sensor using a pipette, followed by amperometric detection at 350 mV and the application of 100 μL of Ringer's solution to flush the WE. Measurements were performed at 1 hr intervals using the same sensor. All measurements were performed at room temperature under ambient conditions.

Statistical analysis: Each data point represents the mean±standard deviation (SD) of three individual measurements. A one-tailed Student's t-test was used for comparison between flat and bent sensors where a p-value <0.05 was considered significant.

Characterizing Embroidered Sensors: A computerized embroidery machine which offers high flexibility in regards to sensor design, configuration and placement was used to fabricate the sensors. In contrast to most wearable textiles, gauze is highly porous and delicate making it difficult to embroider. Therefore, a stabilizer film was used to enhance the rigidity of the gauze which greatly improved the embroidery quality. Additionally, several embroidery parameters were optimizes, such as the thread tension, stitch angle, stitch length and stitch density, to enhance the quality of the electrodes. To accommodate the stretchability of the gauze, the thread tension was adjusted to lowest setting, which minimized tangling of the thread and generated uniform and consistent embroidered patterns. The stitch angle is the angle between the stitching and the horizontal axis (FIG. 2) and influences the weave pattern and robustness of the embroidered features. A stitch angle of 30-45° improved the embroidery quality by increasing the strain of stitches without deforming the underlying gauze. Stitch length and stitch density (FIG. 2) were optimized to 0.5 mm and 0.2 mm, respectively which resulted in good electrode uniformity while minimizing the electrical resistance of the electrodes. Using these optimized parameters, electrochemical sensors were embroidered onto commercial gauze and wound dressing. To demonstrate the flexibility of this approach, electrochemical sensors were fabricated with various geometries and configurations. For example, multiple sensors can be fabricated for multiplexed detection or electrodes with different sizes can be generated to accommodate commercial or custom electrochemical instrumentation. Additionally, sensors can be customized into unique designs, such as symbols or logos, making them less obtrusive and conspicuous.

Figure 7:
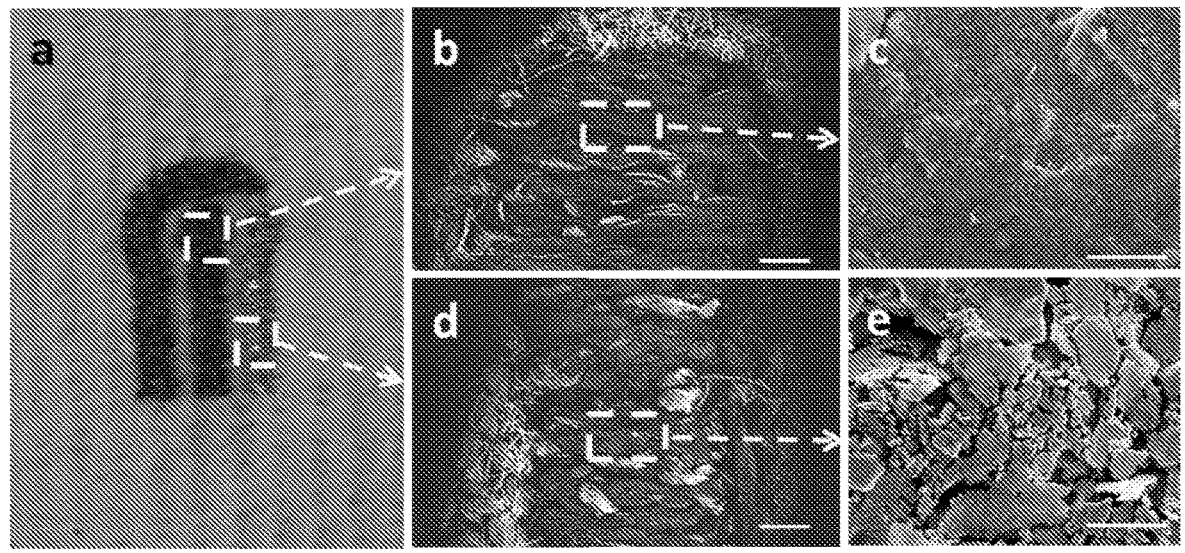
FIG. 7 includes an image of an embroidered electrochemical sensor according to the disclosure on gauze (panel a), SEM images of the WE (panel b) and RE (panel c) at 30× magnification (scale bar, 500 µm.), and close-up SEM images of carbon-coated thread (panel d) and Ag/AgCl-coated thread (panel e) at 5000× magnification (scale bar, 5 µm).

Scanning electron microscopy (SEM) of the working electrode (WE) and reference electrode (RE) was performed to briefly study their surface morphology. From FIG. 7 (panels b, d), the stiches are observed to be tightly-sewn together and firmly integrated into the underlying gauze which enhances the electrical conductivity and robustness of the sensor. Furthermore, the interstitial spacing between the stitches provides a high surface area for the sample thereby enhancing the electrochemical reaction and improving the detection signal. Close-up SEM images of the WE and RE show that the threads are uniformly coated with carbon (FIG. 7, panel c) and Ag/AgCl (FIG. 7, panel e) with good surface coverage even after undergoing the embroidery process.

Figure 8:
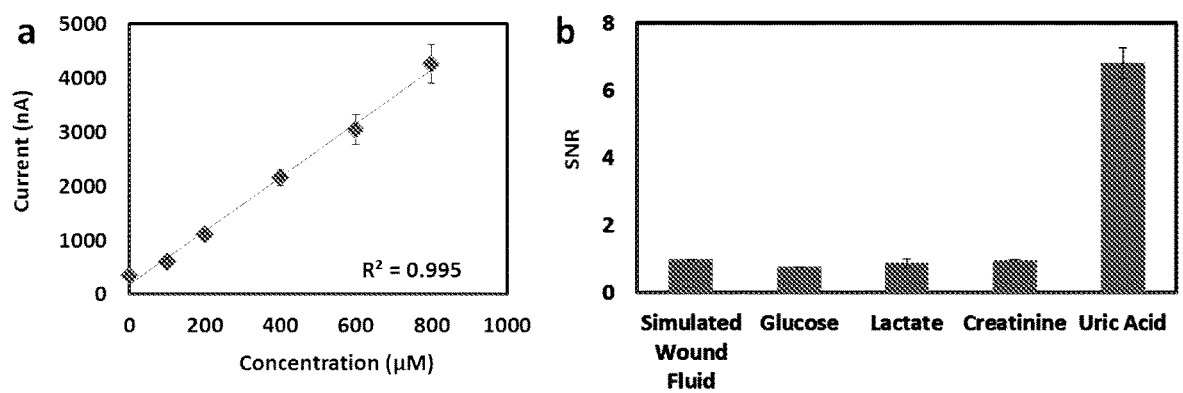
FIG. 8 includes graphs with amperometric measurements of uric acid in simulated wound fluid, with values averaged over the final 10 sec of the detection signal (panel a), and specificity measurements of the uric acid assay using simulated wound fluid samples containing glucose (2 mM), lactate (10 mM), creatinine (120 µM) and uric acid (400 µM), and non-spiked simulated wound fluid, with each bar representing the mean±SD of three separate measurements obtained using new sensors (panel b).

Analytical Performance of Embroidered Gauze Sensors: To evaluate the effectiveness of the embroidered gauze sensor for analytical sensing, it was used for quantitative measurements of uric acid in simulated wound fluid. Samples were dispensed on the backside of the sensor to simulate wound excretion and were quickly absorbed by the sensors due to the high wettability of the thread and gauze. Amperometric measurements were performed after 1 min, which was sufficient time for the sample to be fully absorbed and generate a stable electrochemical reaction. As shown in FIG. 8 (panel a), this uric acid assay exhibits a lower detection limit of 100 μM and a highly linear response (correlation coefficient, $R^2$ of 0.995) over the tested concentration range (100-800 μM) which encompasses the clinically relevant levels in wound patients. In addition, each data point exhibits small SDs of <7% over three individual measurements obtained using new sensors, which demonstrates the high reproducibility of this sensor platform.

The selectivity of the uric acid assay was also tested by performing measurements of samples containing other analytes. These experiments used simulated wound fluid spiked with glucose, lactate, creatinine and uric acid at concentrations of 2 mM, 10 mM, 120 μM and 400 μM, respectively, which is similar to physiological levels found in wound fluid. As shown in FIG. 8 (panel b), only the uric acid sample generated a substantial signal (signal-to-noise ratio, SNR ~7), while the irrelevant targets generated negligible signals similar to that of the non-spiked sample which was used as a blank control. These results suggest that the embroidered gauze sensor is capable of highly specific measurements in complex biofluid samples with a low likelihood of interference caused by nonspecific analytes.

Figure 9:
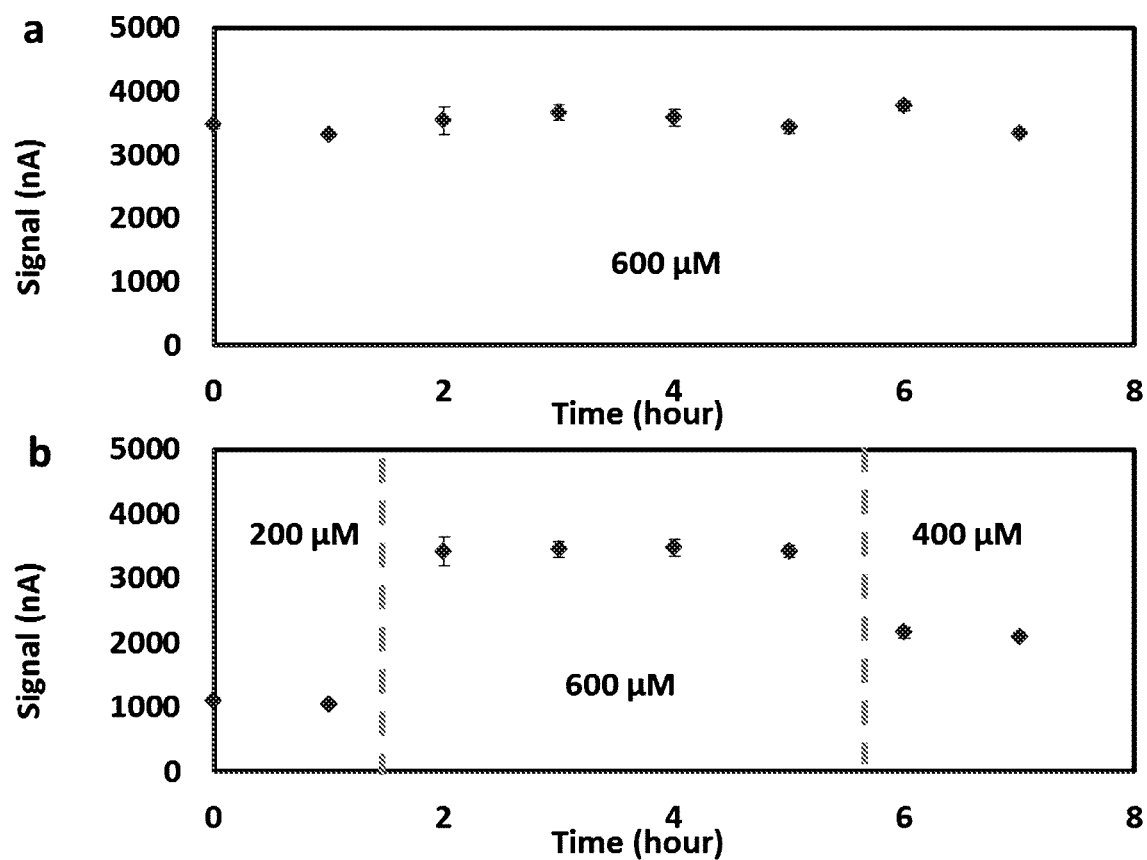
FIG. 9 includes graphs illustrating uric acid monitoring over the course of 7 hr using simulated wound fluid spiked with 600 µM (panel a), and varying concentrations of uric acid (panel b). Each data point represents the mean±SD of three separate measurements using three new sensors.

To evaluate the utility of the gauze sensor for wound monitoring, continuous measurements of uric acid over the course of 7 hr using the same sensor were performed. Uric acid in simulated wound fluid (600 μM) was applied to the sensor every hour followed by amperometric detection. In practice, several layers of gauze are typically wrapped over the wound for adequate coverage and fluid drainage. To mimic this scenario, the sensor was wrapped around a gauze pad and covered with an additional layer of gauze. After each measurement, 100 μL of Ringer's solution was applied to the sensor to flush the sensing region. As shown in FIG. 9 (panel a), the detection signals were consistent throughout the 7 hr experiment exhibiting a small coefficient of variance (COV) of 0.05. These results indicate that the embroidered sensor can generate consistent measurements for several hours which is adequate time between wound dressing changings.

The performance of the sensor in response to dynamic changes in the analyte concentration was tested to more accurately mimic the wound healing process. Specifically, it has been shown that uric acid levels in wound fluid significantly decrease later in the wound healing processing due to catabolysis by microbial uricase. To mimic this scenario, multiple measurements were taken from samples containing different concentrations of uric acid over the course of 7 hr using the same sensor. Samples containing 200 μM were initially dispensed, followed by samples containing 600 μM at hours 2, 3, 4, 5 and 400 μM at hours 6 and 7. As shown in FIG. 9 (panel b), the sensor accurately responded to the dynamic changes of uric acid concentration in the samples. Furthermore, the detection signals are consistent with those generated from single measurements (FIG. 8, panel a) even after being exposed to multiple samples with varying concentrations. These results indicate that the gauze sensor offers excellent accuracy and repeatability, making it suitable for wound monitoring.

Figure 10:
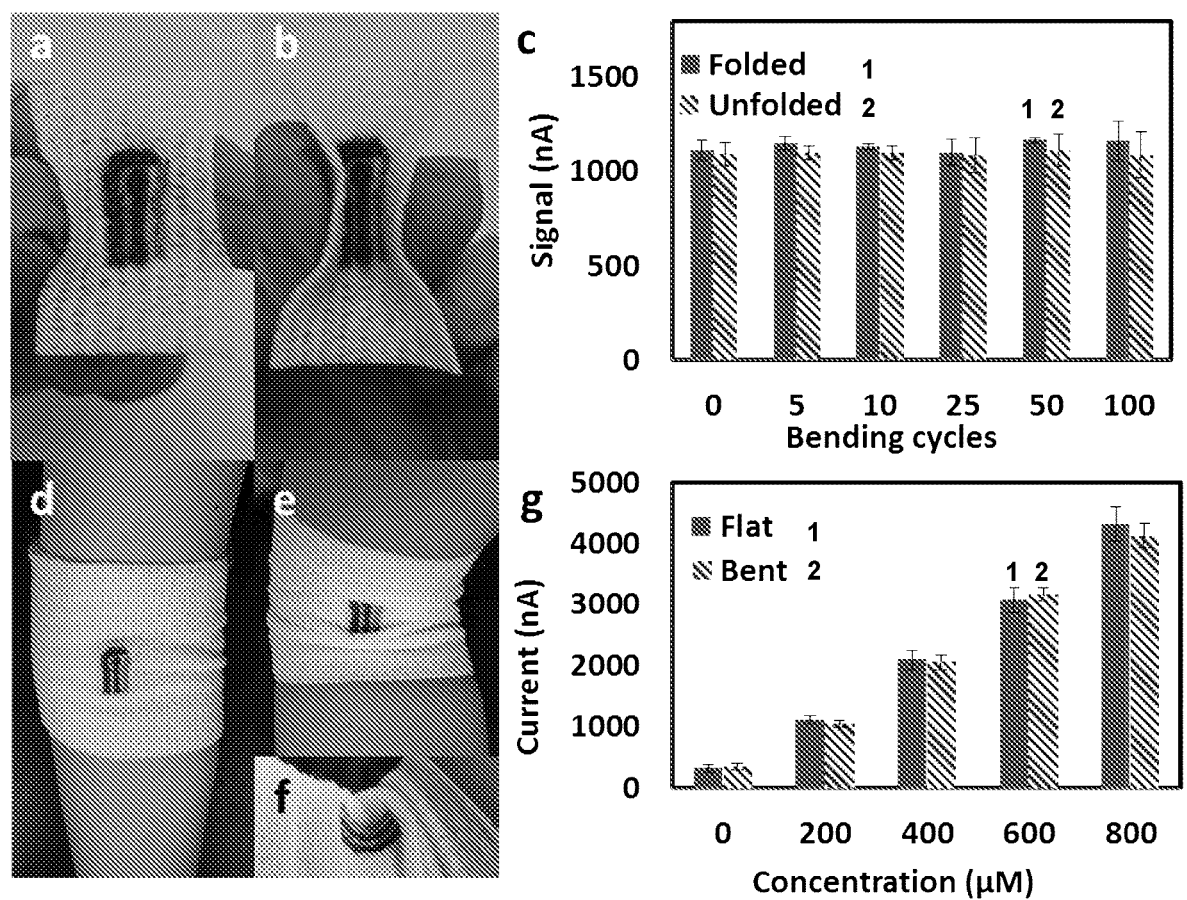
FIG. 10 includes images illustrating bend testing of the embroidered gauze sensor before (panel a) and after (panel b) folding, amperometric measurements of uric acid (200 µM) in simulated wound fluid using folded (solid) and unfolded (striped) sensors (panel c), images of the sensor positioned flat (panel d) and bent at 90° (panels e, f) while wrapped around an arm, and amperometric measurements of uric acid in simulated wound fluid using flat (solid) or bent (striped) sensors (panel g). Each bar represents the mean±SD of three separate measurements using new sensors.

Sensor Durability Testing: An important consideration for wearable sensors is the influence of mechanical deformation on the analytical performance. To evaluate the mechanical durability of the embroidered gauze sensor, the sensor was manually folded and flattened for up to 100 cycles (FIG. 10, panels a, b), then used to perform measurements of uric acid (200 μM) in simulated wound fluid at intervals of 5, 10, 25, 50 and 100 bending cycles. Measurements were also performed at the same intervals using sensors that did not undergo folding. By comparing the detection signals from folded and unfolded sensors (FIG. 10, panel c), no significant difference ($p>0.292$) was found in the analytical performance due to mechanical deformation for up to 100 bending cycles. To mimic the mechanical stress on the sensor due to the wearer's movement, the analytical performance in response to deformation occurring simultaneously while the measurement was carried out was. Amperometric measurements of uric acid in simulated wound fluid were performed using sensors that were positioned flat (FIG. 10, panel d) and bent at 90° (FIG. 10, panels e, f) while the signal was being recorded. As shown in FIG. 5 (panel g), there is no significant difference (p>0.181) in the detection performance between the two sets of sensors from 0-800 µM. Furthermore, the signals generated from the bent sensors maintained a highly linear response ($R^2$=0.994) similar to those of the flat sensors with low SDs across multiple measurements using new sensors. This collective data show that mechanical deformation has a minimal impact on the performance of the embroidered gauze sensor, suggesting that it will be able to maintain high accuracy and reproducibility under instances of repeated deformation for wearable sensing applications.

Figure 11:
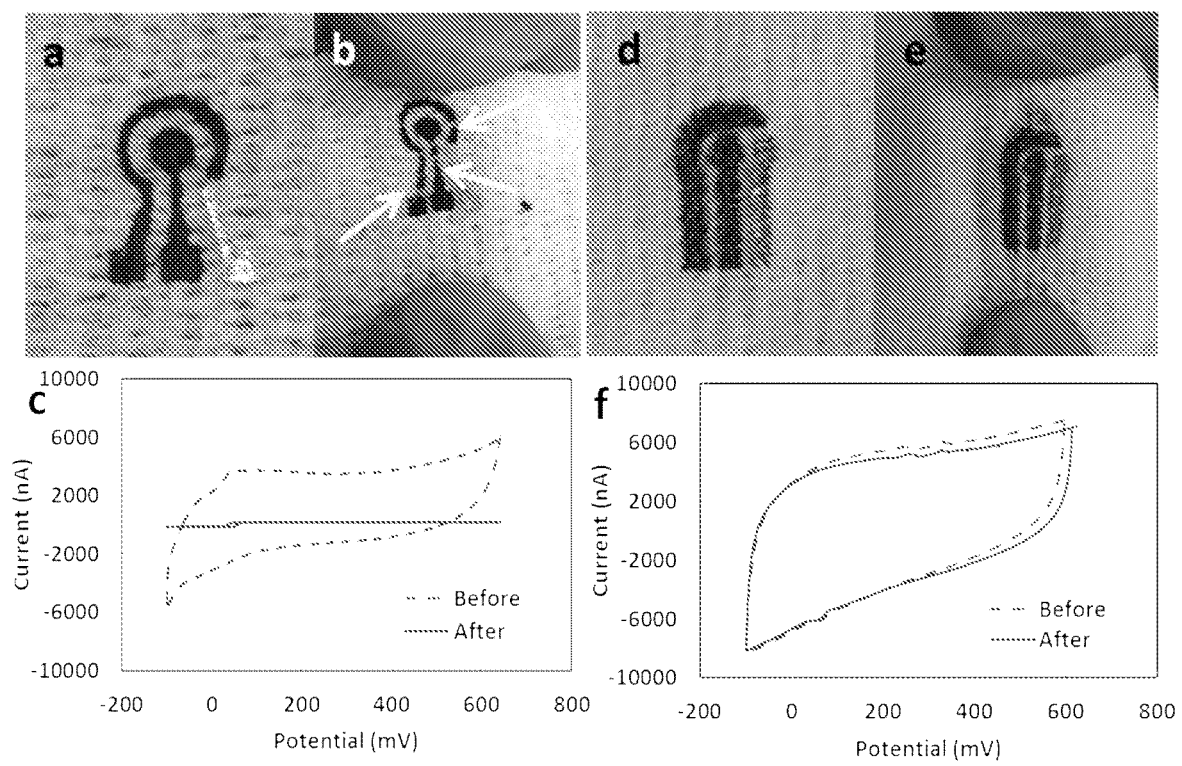
FIG. 11 illustrates a comparison of screen-printed and embroidered gauze sensors in response to mechanical stretching, including images of a screen-printed sensor before (panel a) and after (panel b) stretching (with arrows indicating electrode cracking due to stretching), and corresponding cyclic voltammetry measurements (panel c).

The mechanical resilience of the embroidered gauze sensor was evaluated and compared with a screen-printed sensor by subjecting both sensors to mechanical stretching as shown in FIG. 11. While sensors can be screen-printed on gauze (FIG. 11, panel a), the electrodes begin to crack after a stretching force of 2.6 N (FIG. 11, panel b). In contrast, there was no observable damage to the embroidered sensor (FIG. 11, panel d) at the same stretching force. Upon further stretching, the embroidered electrodes remained intact with no damage even as the gauze began to tear (FIG. 11, panel e). Cyclic voltammetry was used to investigate the electrochemical performance of both sensors in response to mechanical stretching. Prior to stretching, the cyclic voltammogram of the screen-printed sensor shows good electroactivity and similar performance (i.e., reversibility, anodic peak currents) as the embroidered sensor. However, the screen-printed sensor exhibits significant loss of functionality after stretching generating a nearly zero response signal (FIG. 11, panel c). In contrast, the cyclic voltammograms of the embroidered gauze sensor before and after stretching are nearly identical indicating that it exhibits excellent resilience against mechanical stretching (FIG. 11, panel f).

Summary: This example illustrates an embroidery method to fabricate robust, flexible electrochemical sensors on gauze for rapid analytical measurements. This approach offers high flexibility and customization in regards to sensor design and configuration, and is readily amenable to existing manufacturing processes (i.e. embroidery) using off-the-shelf materials (i.e. thread, gauze). Single and continuous measurements of uric acid in simulated wound fluid shows that this sensor offers excellent analytical performance for both in vitro testing and wound monitoring. Experiments to evaluate the durability of the sensor showed its ability to generate consistent and accurate results in response to repeated folding/bending before and during measurements, and exhibit superior resilience against mechanical strain and deformation. These collective features make the embroidered gauze sensor a promising technology for wearable applications requiring rapid, accurate measurements on a disposable platform.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed is:

1. An embroidered electrochemical sensor for detecting a target analyte, the sensor comprising:
   (a) a flexible substrate;
   (b) a working electrode (WE) embroidered on the flexible substrate, the working electrode comprising a first textile fiber core and a first electrically conductive material shell around the first textile fiber core;
   (c) optionally a counter electrode (CE) embroidered on the flexible substrate and spaced apart from the working electrode, the counter electrode comprising a second textile fiber core and a second electrically conductive material shell around the second textile fiber core;
   (d) a reference electrode (RE) embroidered on the flexible substrate and spaced apart from both the working electrode and the counter electrode, the reference electrode comprising a third textile fiber core and a third electrically conductive material shell around the third textile fiber core; and
   (e) an enzyme probe bound to the working electrode, wherein the enzyme probe is specific to the target analyte.

2. The sensor of claim 1, wherein the flexible substrate is a textile substrate.

3. The sensor of claim 2, wherein the textile substrate comprises a textile material selected from the group consisting of animal-based textile material, plant-based textile materials, synthetic textile materials, and combinations thereof.

4. The sensor of claim 2, wherein the textile substrate comprises a textile material selected from the group consisting of wools, cottons, denim, silk, satin, bamboo, polyesters, leather, artificial leather, polyacrylonitrile, polyamides, polyurethanes, polyolefins, polychloroprenes, and combinations thereof.

5. The sensor of claim 2, wherein the textile substrate is a component of or attached to a garment or wearable item.

6. The sensor of claim 1, wherein the first textile fiber core, the second textile fiber core, and the third textile fiber core are independently selected from the group consisting of animal-based textile fibers, plant-based textile fibers, synthetic textile fibers, and combinations thereof.

7. The sensor of claim 1, wherein the first textile fiber core, the second textile fiber core, and the third textile fiber core are independently selected from the group consisting of wools, cottons, denim, silk, satin, bamboo, polyesters, leather, artificial leather, polyacrylonitrile, polyamides, polyurethanes, polyolefins, polychloroprenes, and combinations thereof.

8. The sensor of claim 1, wherein first electrically conductive material shell, the second electrically conductive material shell, and the third electrically conductive material shell are independently selected from the group consisting of a metal-containing coating, a carbon-containing coating, a conductive polymer-containing coating, and combinations thereof.

9. The sensor of claim 1, wherein:
   (i) the first electrically conductive material shell and the second electrically conductive material shell each independently comprise a carbon-containing coating; and
   (ii) the third electrically conductive material shell comprises a metal-containing coating.

10. The sensor of claim 1, wherein a fiber of the working electrode, a fiber of the counter electrode, and a fiber of the reference electrode each independently have an electrical resistance ranging from 0.1 Ω/cm to 1000 Ω/cm.

11. The sensor of claim 1, wherein a fiber of the working electrode and a fiber of the counter electrode each independently have an electrical resistance greater than that of a fiber of the reference electrode.

12. The sensor of claim 11, wherein:
   (i) a fiber of the working electrode and a fiber of the counter electrode each independently have an electrical resistance ranging from 20 Ω/cm to 1000 Ω/cm; and
   (ii) a fiber of the reference electrode has an electrical resistance ranging from 0.1 Ω/cm to 100 Ω/cm.

13. The sensor of claim 1, wherein the enzyme probe comprises an oxidoreductase enzyme capable of catalyzing an oxidation-reduction (redox) reaction with the target analyte.

14. The sensor of claim 1, wherein the enzyme probe comprises glucose oxidase and the target analyte is glucose.

15. The sensor of claim 1, wherein the enzyme probe comprises lactate oxidase and the target analyte is lactate.

16. The sensor of claim 1, wherein the enzyme probe comprises uricase and the target analyte is uric acid.

17. The sensor of claim 1, comprising the counter electrode.

18. The sensor of claim 1, wherein the working electrode, the counter electrode, and the reference electrode each are embroidered having (i) a stitch angle ranging from 30° to 45°, (ii) a stitch distance ranging from 0.1 mm to 0.3 mm, and (iii) a stitch length ranging from 0.4 mm to 0.6 mm.

19. The sensor of claim 1, wherein the flexible substrate is not a woven substrate.

20. The sensor of claim 1, wherein the flexible substrate is free from silk.

21. A multiplexed embroidered electrochemical sensor for detecting two or more target analytes, the sensor comprising:
   (a) a first embroidered electrochemical sensor according to claim 1, wherein the first sensor comprises a first enzyme probe specific to a first target analyte; and
   (b) a second embroidered electrochemical sensor according to claim 1, wherein the second sensor comprises a second enzyme probe different from the first enzyme probe and specific to a second target analyte different from the first target analyte;
   wherein the flexible substrate of the first sensor can be the same or different from that of the second sensor.

22. A multiplexed embroidered electrochemical sensor kit for detecting two or more target analytes, the kit comprising:
   (a) a first embroidered electrochemical sensor according to claim 1, wherein the first sensor comprises a first flexible substrate and a first enzyme probe specific to a first target analyte; and
   (b) a second embroidered electrochemical sensor according to claim 1, wherein the second sensor comprises a second flexible substrate separate from the first flexible substrate and a second enzyme probe different from the first enzyme probe and specific to a second target analyte different from the first target analyte.

23. A method for detecting a target analyte, the method comprising:
   (a) providing the embroidered electrochemical sensor according to claim 1;
   (b) applying a sample containing or suspected of containing the target analyte to the working electrode and allowing sufficient time for reaction of any target analyte with the enzyme probe; and
   (c) electrochemically detecting the target analyte, if present.

24. The method of claim 23, wherein the sensor is in a flat configuration during sample application and electrochemical detection.

25. The method of claim 23, wherein the sensor is in a non-flat configuration during sample application and electrochemical detection.

26. The method of claim 23, wherein the sensor has undergone periodic deformation prior to sample application and electrochemical detection.

27. The method of claim 23, wherein the sample contains the target analyte.

28. The method of claim 23, wherein the sample comprises one or more non-target analyte components selected from the group consisting of biological fluids, components thereof, and combinations thereof.

29. The method of claim 23, wherein the sample comprises a liquid medium.

30. The method of claim 23, wherein electrochemical detection comprises applying a voltage differential to the sensor and measuring a corresponding electrical current though the sensor.

31. The method of claim 23, further comprising:
   (d) quantitatively determining the amount of the target analyte in the sample.

* * * * *